(12) United States Patent
Sheppeck et al.

(10) Patent No.: US 7,211,671 B2
(45) Date of Patent: May 1, 2007

(54) SUBSTITUTED 1,3-DIHYDRO-IMIDAZOL-2-ONE AND 1,3-DIHYDRO-IMIDAZOL-2-THIONE DERIVATIVES AS INHIBITORS OF MATRIX METALLOPROTEINASES AND/OR TNF-α CONVERTING ENZYME (TACE)

(75) Inventors: James Sheppeck, Newtown, PA (US); John L. Gilmore, Yardley, PA (US); Xiao-Tao Chen, Furlong, PA (US); Xiaohua He, Hockessin, DE (US)

(73) Assignee: Bristol Myers Squibb Company, Princeton, NJ (US)

( * ) Notice: Subject to any disclaimer, the term of this patent is extended or adjusted under 35 U.S.C. 154(b) by 255 days.

(21) Appl. No.: 10/946,418

(22) Filed: Sep. 21, 2004

(65) Prior Publication Data

US 2005/0075384 A1    Apr. 7, 2005

Related U.S. Application Data

(60) Provisional application No. 60/507,556, filed on Oct. 1, 2003.

(51) Int. Cl.
*C07D 401/12* (2006.01)
(52) U.S. Cl. ............... 546/152; 548/316.4; 548/325.1
(58) Field of Classification Search ............... 546/152; 548/325.1, 316.4
See application file for complete search history.

(56) References Cited

U.S. PATENT DOCUMENTS

2003/0130273 A1    7/2003    Sheppeck et al.

OTHER PUBLICATIONS

Glaβ et al., Archiv der Pharmazie (Weinheim, Germany) (1995), 328(10), pp. 709-719.*

* cited by examiner

*Primary Examiner*—Laura L. Stockton
(74) *Attorney, Agent, or Firm*—Jing G. Sun

(57) ABSTRACT

The present invention describes novel 1,3-dihydro-imidazol-2-one or 1,3-dihydro-imidazol-2-thione compounds of formula (I):

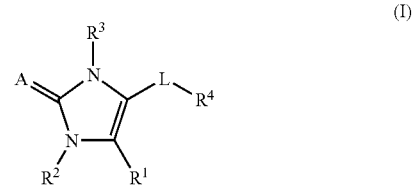

(I)

or a stereoisomer or pharmaceutically acceptable salt or solvate thereof, wherein A, L $R^1$, $R^2$, $R^3$ and $R^4$ are defined in the present specification, which are useful as selective inhibitors of MMP, TACE, aggrecanase or a combination thereof. This invention also relates to pharmaceutical compositions comprising these compounds and methods of using the same.

12 Claims, No Drawings

SUBSTITUTED 1,3-DIHYDRO-IMIDAZOL-2-ONE AND 1,3-DIHYDRO-IMIDAZOL-2-THIONE DERIVATIVES AS INHIBITORS OF MATRIX METALLOPROTEINASES AND/OR TNF-α CONVERTING ENZYME (TACE)

CROSS-REFERENCE TO RELATED APPLICATIONS

The present application claims the priority benefit of U.S. Provisional Application No. 60/507,556, filed Oct. 1, 2003, which is expressly incorporated fully herein by reference.

FIELD OF THE INVENTION

The present invention relates generally to compounds that inhibit matrix metalloproteinases (MMP), TNF-α converting enzyme (TACE), aggrecanase or a combination thereof. In particular it is directed to novel 1,3-dihydro-imidazol-2-one or 1,3-dihydro-imidazol-2-thione compounds of formula (I):

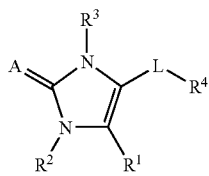

or a stereoisomer or pharmaceutically acceptable salt or solvate thereof, which are useful as selective inhibitors of MMP, TACE, aggrecanase or a combination thereof. This invention also relates to pharmaceutical compositions comprising these compounds and methods of using the same.

BACKGROUND OF THE INVENTION

There is now a body of evidence that metalloproteases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMPs (tissue inhibitors of metalloprotease), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. *J. Bone Joint Surg.* 1970, 52A, 424–434). There are four classes of protein degradative enzymes in mammalian cells: serine, cysteine, aspartic and metalloproteases. The available evidence supports that it is the metalloproteases that are responsible for the degradation of the extracellular matrix of articular cartilage in OA and RA.

Increased activities of collagenases and stromelysin have been found in OA cartilage and the activity correlates with severity of the lesion (Mankin et al. *Arthritis Rheum.* 1978, 21, 761–766, Woessner et al. *Arthritis Rheum.* 1983, 26, 63–68 and Woessner et al. *Arthritis Rheum.* 1984, 27, 305–312). In addition, aggrecanase has been identified as providing the specific cleavage product of proteoglycan found in RA and OA patients (Lohmander L. S. et al. *Arthritis Rheum.* 1993, 36, 1214–22).

Therefore, metalloproteases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. *Ann. Rep. Med. Chem.* 1990, 25, 175–184, AP, San Diego).

Tumor necrosis factor-α (TNF-α) is a cell-associated cytokine that is processed from a 26 kd precursor form to a 17 kd active form. TNF-α has been shown to be a primary mediator in humans and in animals, of inflammation, fever, and acute phase responses, similar to those observed during acute infection and shock. Excess TNF-α has been shown to be lethal. There is now considerable evidence that blocking the effects of TNF-α with specific antibodies can be beneficial in a variety of circumstances including autoimmune diseases such as rheumatoid arthritis (Feldman et al. *Lancet* 1994, 344, 1105), non-insulin dependent diabetes melitus (Lohmander, L. S. et al. *Arthritis Rheum.* 1993, 36, 1214–22) and Crohn's disease (MacDonald et al. *Clin. Exp. Immunol.* 1990, 81, 301).

Compounds which inhibit the production of TNF-α are therefore of therapeutic importance for the treatment of inflammatory disorders. Recently, TNF-α converting enzyme (TACE), the enzyme responsible for TNF-α release from cells, were purified and sequenced (Black et al. *Nature* 1997, 385, 729; Moss et al. *Nature* 1997, 385, 733). This invention describes molecules that inhibit this enzyme and hence the secretion of active TNF-α from cells. These novel molecules provide a means of mechanism based therapeutic intervention for diseases including but not restricted to septic shock, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, OA, RA, multiple sclerosis, radiation damage, hyperoxic alveolar injury, periodontal disease, HIV and non-insulin dependent diabetes melitus.

Since excessive TNF-α production has been noted in several disease conditions also characterized by MMP-mediated tissue degradation, compounds which inhibit both MMPs and TNF-α production may also have a particular advantage in diseases where both mechanisms are involved.

Prostaglandins (PG) play a major role in the inflammation process and the inhibition of PG production has been a common target of anti-inflammatory drug discovery. Many NSAIDS have been found to prevent the production of PG by inhibiting the enzyme cyclooxygenase (COX). Among the two isoforms of COXs, COX-1 is constitutively expressed. COX-2 is an inducible isozyme associated with inflammation. Selective COX-2 inhibitor was believed to maintain the efficacy of traditional NSAIDs, which inhibit both isozymes, and produce fewer and less drastic side effects. As a result, development of selective COX-2 inhibitors has attracted major interest in the pharmaceutical industry. Because of the significant roles of PGs and TNF-α in inflammation, combined use of COX-2 and TACE inhibitors may have superior efficacy to either therapy alone in some inflammatory diseases.

Human macrophage elastase (MMP-12) is expressed primarily by alveolar macrophages and is responsible for tissue remodelling by proteolytically degrading elastin. MMP-12 knockout mice appear to have a diminished capacity to degrade elastin, particularly in lung tissue, and appear less susceptible to pulmonary diseases such as emphysema (Hautamaki et al. *Science* 1997, 277, 2002–2004; Lanone et al. *J. Clin. Invest.* 2002, 110, 463–474). This invention describes molecules that inhibit the activity of MMP-12 and may circumvent undesired tissue destruction found in a variety of human diseases. These novel molecules provide a means of mechanism based therapeutic intervention for diseases including but not restricted to: emphysema, asthma, chronic obstructive pulmonary disease, cystic fibrosis, cancer, metastatic disease, atherosclerosis, and aneurysm.

It is desirable to find new compounds with improved pharmacological characteristics compared with known MMP and/or TACE inhibitors. For example, it is preferred to find new compounds with improved MMP and/or TACE inhibitory activity and selectivity for an MMP and/or TACE versus other metalloproteases. It is also desirable and preferable to find compounds with advantageous and improved characteristics in one or more of the following categories: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

The compounds of the present invention act as inhibitors of MPs, in particular TACE, MMPs, and/or aggrecanase. These novel molecules are provided as anti-inflammatory compounds and cartilage protecting therapeutics. The inhibition of aggrecanase, TACE, and other metalloproteases by molecules of the present invention indicates they are anti-inflammatory and should prevent the degradation of cartilage by these enzymes, thereby alleviating the pathological conditions of OA and RA.

SUMMARY OF THE INVENTION

Accordingly, the present invention provides novel 1,3-dihydro-imidazol-2-one or 1,3-dihydro-imidazol-2-thione compounds, and analogues thereof, which are useful as MMP, TACE and/or aggrecanase inhibitors, or stereoisomers or pharmaceutically acceptable salts, solvates, or prodrugs thereof.

The present invention also provides pharmaceutical compositions comprising a pharmaceutically acceptable carrier and a therapeutically effective amount of at least one of the compounds of the present invention, or a stereoisomer or a pharmaceutically acceptable salt, solvate, or prodrug thereof.

The present invention also provides a method for modulation of the coagulation cascade comprising administering to a host in need of such treatment a therapeutically effective amount of at least one of the compounds of the present invention, or a stereoisomer or a pharmaceutically acceptable salt, solvate, or prodrug thereof.

The present invention also provides a method for treating inflammatory disorders comprising: administering to a host in need of such treatment a therapeutically effective amount of at least one of the compounds of the present invention, or a stereoisomer or a pharmaceutically acceptable salt, solvate, or prodrug thereof.

The present invention provides a method of treating a condition or disease mediated by MMPs, TACE, aggrecanase, or a combination thereof in a mammal, comprising: administering to the mammal in need of such treatment a therapeutically effective amount of a compound of the present invention, or a stereoisomer or a pharmaceutically acceptable salt, solvate, or prodrug thereof.

The present invention provides a method comprising: administering a compound of the present invention, or a stereoisomer or a pharmaceutically acceptable salt, solvate, or prodrug thereof, in an amount effective to treat a condition or disease mediated by MMPs, TACE, aggrecanase, or a combination thereof.

The present invention also provides novel 1,3-dihydro-imidazol-2-one or 1,3-dihydro-imidazol-2-thione compounds, and analogues thereof, for use in therapy.

The present invention also provides the use of 1,3-dihydro-imidazol-2-one or 1,3-dihydro-imidazol-2-thione compounds, and analogues thereof, for the manufacture of a medicament for the treatment of a thromboembolic disorder.

The present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

The present invention provides a medical device for implanting into a mammalian body wherein the medical device has a coating material comprising an amount of one of the compounds of the present invention or a pharmaceutically-acceptable salt, hydrate, or prodrug thereof, effective for reducing inflammation or restinosis. Preferably, the implantable medical device is a stent.

These and other embodiments, which will become apparent during the following detailed description, have been achieved by the inventors' discovery that the presently claimed novel compounds of the present invention, or pharmaceutically acceptable salt or prodrug forms thereof, are effective inhibitors of MMP, TACE and/or aggrecanase.

DETAILED DESCRIPTION OF PREFERRED EMBODIMENTS

In a first aspect, the present invention provides, inter alia, compounds of Formula (I):

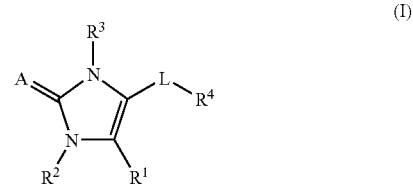

or a stereoisomer or pharmaceutically acceptable salt or solvate thereof, wherein:

A is O or S;

L is a bond, CO, CH(OH), or $CR^5R^6$;

$R^1$ is Q, F, Cl, Br, I, CN, $NO_2$, —$CF_2CF_3$, —$NR^7R^8$, $C_{1-4}$ haloalkyl, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$—Q, —$(CR^aR^{a1})_tNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_tOC(O)O(CR^aR^{a1})_s$—Q, —$(CR^aR^{a1})_tOC(O)NR^a(CR^aR^{a1})_s$—Q, —$(CR^aR^{a1})_tNR^aC(O)O(CR^aR^{a1})_s$—Q, —$(CR^aR^{a1})_rNR^aC(O)NR^a(CR^aR^{a1})_s$—Q, —$(CR^aR^{a1})_rS(CR^aR^{a1})_s$—Q, —$(CR^aR^{a1})_rS(O)(CR^aR^{a1})_s$—Q, —$(CR^aR^{a1})_rS(O)_2(CR^aR^{a1})_s$—Q, —$(CR^aR^{a1})_rSO_2NR^a(CR^aR^{a1})_s$—Q, —$(CR^aR^{a1})_rNR^aSO_2$—$(CR^aR^{a1})_s$—Q, or —$(CR^aR^{a1})_rNR^aSO_2NR^a(CR^aR^{a1})_s$—Q;

$R^2$ is H, $C_{1-4}$ alkyl, $C_{2-4}$ alkenyl, or $C_{2-4}$ alkynyl;

$R^3$ is H, $C_{1-4}$ alkyl, $C_{2-4}$ alkenyl, or $C_{2-4}$ alkynyl;

$R^4$ is —$Z^0$—W—U—X—Y—Z—$U^a$—$X^a$—$Y^a$—$Z^a$;

$R^5$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$—Q, —$(CR^aR^{a1})_rNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_rOC(O)O(CR^aR^{a1})_s$—Q, —$(CR^aR^{a1})_rOC(O)NR^a(CR^aR^{a1})_s$—Q, —$(CR^aR^{a1})_rNR^aC(O)O(CR^aR^{a1})_s$—Q, —$(CR^aR^{a1})_rNR^aC(O)NR^a(CR^aR^{a1})_s$—Q, —$(CR^aR^{a1})_rS(O)_p(CR^aR^{a1})_s$—Q, —$(CR^aR^{a1})_rSO_2NR^a(CR^aR^{a1})_s$—Q, —$(CR^aR^{a1})_rNR^aSO_2$—$(CR^aR^{a1})_s$—Q, or —$(CR^aR^{a1})_rNR^aSO_2NR^a(CR^aR^{a1})_s$—Q;

$R^6$ is Q, —$C_{1-6}$ alkylene-Q, —$C_{2-6}$ alkenylene-Q, —$C_{2-6}$ alkynylene-Q, —$(CR^aR^{a1})_rO(CR^aR^{a1})_s$—Q, —$(CR^aR^{a1})_rNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_rS(O)_p(CR^aR^{a1})_s$—Q, —$(CR^aR^{a1})_rSO_2NR^a(CR^aR^{a1})_s$—Q, or —$(CR^aR^{a1})_rNR^aSO_2$—$(CR^aR^{a1})_s$—Q;

$R^7$ is H, $C_{1-6}$ alkyl, $C_{2-6}$ alkenyl, $C_{2-6}$ alkynyl, —$C_{1-6}$ alkylene-$Q^1$, —$C_{2-6}$ alkenylene-$Q^1$, —$C_{2-6}$ alkynylene-$Q^1$, —$(CR^aR^{a1})_rC(O)(CR^aR^{a1})_s$—$Q^1$, —$(CR^aR^{a1})_rC(O)O(CR^aR^{a1})_s$—$Q^1$, —$(CR^aR^{a1})_rC(O)O(CR^aR^{a1})_rOC(O)$—$Q^1$, —$(CR^aR^{a1})_rC(O)NH(CR^aR^{a1})_s$—$Q^1$, or —$(CR^aR^{a1})_rS(O)_2)(CR^aR^{a1})_s$—$Q^1$;

$R^8$ is H, $C_{1-6}$ alkyl, or —$(CH_2)_n$-phenyl;

alternatively, $R^7$ and $R^8$ combine to form a 5–10 membered heterocyclic ring consisting of carbon atoms and 0–2 additional heteroatoms selected from the group consisting of N, O, and $S(O)_p$;

each $R^9$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rC(S)NR^aR^{a1}$, —$(CR^aR^{a1})_rNR^aC(O)R^{a1}$, —$(CR^aR^{a1})_tOC(O)NR^aR^{a1}$, —$(CR^aR^{a1})_rNR^aC(O)OR^{a1}$, —$(CR^aR^{a1})_tNR^aC(O)NR^aR^{a1}$, —$(CR^aR^{a1})_rS(O)R^{a3}$, —$(CR^aR^{a1})_sS(O)R^{a3}$, —$(CR^aR^{a1})_rS(O)_2R^{a3}$, —$(CR_aR_{a1})SO_2NR^aR^{a1}$, —$(CR^aR^{ai})_rNR^aSO_2R^{a3}$, —$(CR^aR^{a1})_tNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$; or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

each $R^{10}$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(S)OR^{a1}$, —$(CR^aR^{a1})_rC(O)NR^aR^{a1}$, —$(CR^aR^{a1})_rC(S)NR^aR^{a1}$, —$(CR^aR^{a1})_rNR^aC(O)R^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)R^{a3}$, —$(CR^aR^{a1})_rS(O)R^{a3}$, —$(CR^aR^{a1})_rS(O)_2R^{a3}$, —$(CR^aR^{a1})_rSO_2NR^aR^{a1}$, —$(CR^aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$; or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

each Q is, independently at each occurrence, H, $CF_3$, —$CH_2F$, —$CHF_2$, $C_{1-6}$ alkyl, a $C_{3-13}$ carbocycle substituted with 0–5 $R^d$, or a 5–12 membered heterocycle consisting of carbon atoms and 1–4 heteroatoms selected from the group consisting of $NR^9$, O, and $S(O)_p$, and substituted with 0–5 $R^d$;

each $Q^1$ is, independently at each occurrence, $C_{1-6}$ alkyl, a $C_{3-13}$ carbocycle substituted with 0–5 $R^d$, or a 5–12 membered heterocycle consisting of carbon atoms and 1–4 heteroatoms selected from the group consisting of $NR^9$, O, and $S(O)_p$, and substituted with 0–5 $R^d$;

$Z^0$ is aryl or a 5–6 membered heteroaryl consisting of carbon atoms and 0–3 ring heteroatoms selected from O, N, $NR^9$, and S, and substituted with 0–3 $R^{10}$; and the aryl or heteroaryl is optionally fused to a 5–6 membered carbocycle or heterocycle consisting of carbon atoms and 0–2 ring heteroatoms selected from O, N, $NR^9$, and $S(O)_p$, and 0–2 double bonds, and substituted with 0–3 $R^{10}$;

W is $(CR_aR_{a1})_m$, $C_{2-3}$ alkenylene, or $C_{2-3}$ alkynylene;

U is O, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, or $NR^{a1}SO_2NR^{a1}$;

X is a bond, $C_{1-3}$ alkylene, $C_{2-3}$ alkenylene, or $C_{2-3}$ alkynylene;

Y is a bond, O, $NR^{a1}$, $S(O)_p$, or C(O);

alternatively, $Z^0$ is absent, and W—U—X—Y forms $S(O)_p$;

Z is a $C_{3-13}$ carbocycle substituted with 0–5 $R^b$, or a 5–14 membered heterocycle consisting of carbon atoms and 1–4 heteroatoms selected from the group consisting of N, O, and $S(O)_p$ and substituted with 0–5 $R^b$;

$U^a$ is a bond, O, $NR^{a1}$, C(O), $CR^a(OH)$, C(O)O, OC(O), $C(O)NR^{a1}$, $NR^{a1}C(O)$, OC(O)O, $OC(O)NR^{a1}$, $NR^{a1}C(O)O$, $NR^{a1}C(O)NR^{a1}$, $S(O)_p$, $S(O)_pNR^{a1}$, $NR^{a1}S(O)_p$, or $NR^{a1}SO_2NR^{a1}$;

$X^a$ is a bond, $C_{1-10}$ alkylene, $C_{2-10}$ alkenylene, or $C_{2-10}$ alkynylene;

$Y^a$ is a bond, O, $NR^{a1}$, $S(O)_p$, or C(O);

$Z^a$ is a $C_{3-13}$ carbocycle substituted with 0–5 $R^c$, or a 5–14 membered heterocycle consisting of carbon atoms and 1–4 heteroatoms selected from the group consisting of N, O, and $S(O)_p$ and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

each $R^a$ is, independently at each occurrence, H, $C_{1-6}$ alkyl, phenyl, or benzyl;

each $R^{a1}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$—3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

alternatively, $R^a$ and $R^{a1}$ when attached to a nitrogen, together with the nitrogen to which they are attached, combine to form a 5 or 6 membered heterocycle consisting of carbon atoms and from 0–1 additional heteroatoms selected from N, $NR^{a2}$, O, and $S(O)_p$;

each $R^{a2}$ is, independently at each occurrence, $C_{1-4}$ alkyl, phenyl, or benzyl;

each $R^{a3}$ is, independently at each occurrence, H, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, or —$(CH_2)_r$-3–8 membered carbocyclic or heterocyclic ring consisting of carbon atoms and 0–2 ring heteroatoms selected from N, $NR^{a2}$, O, and $S(O)_p$, and substituted with 0–3 $R^{c1}$;

each $R^b$ is, independently at each occurrence, $C_{1-6}$ alkyl substituted with 0–1 $R^{c1}$, $OR^a$, $SR^a$, Cl, F, Br, I, =O, —CN, $NO_2$, $NR^aR^{a1}$, $C(O)R^a$, —$C(O)OR^a$, —$C(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, $S(O)_pR^{a3}$, $CF_3$, $CF_2CF_3$, $CHF_2$, $CH_2F$, or phenyl;

each $R^c$ is, independently at each occurrence, H, Cl, F, Br, I, =O, CN, $NO_2$, $CF_3$, $CF_2CF_3$, $CH_2F$, $CHF_2$, —$(CR^aR^{a1})_rOR^a$, —$(CR^aR^{a1})_rNR^aR^{a1}$, —$(CR^aR^{a1})_rC(=NCN)NR^aR^{a1}$, —$(CR^aR^{a1})_rC(=NR^a)NR^aR^{a1}$, —$(CR^aR^{a1})_rC(=NOR^a)NR^aR^{a1}$, —$(CR^aR^{a1})_rC(O)NR^aOH$, —$(CR^aR^{a1})_rC(O)R^{a1}$, —$(CR^aR^{a1})_rC(O)OR_{a1}$, —$(CR^aR^{a1})_rC(S)OR^{a1}$, —$(CR^aR^{a1})_rC(O)NR^aR^{a1}$, —$(CR^aR^{a1})_rNR^aC(O)R^{a1}$, —$(CR^aR^{a1})_rC(S)NR^aR^{a1}$, —$(CR^aR^{a1})_rOC(O)NR^aR^{a1}$, —$(CR^aR^{a1})_rNR^aC(O)OR^{a1}$, —$(CR^aR^{a1})_rNR^aC(O)NR^aR^{a1}$, —$(CR^aR^{a1})_rS(O)_pR^{a3}$, —$(CR^aR^{a1})_rSO_2NR_aR_{a1}$, —$(CR_aR^{a1})_rNR^aSO_2R^{a3}$, —$(CR^aR^{a1})_rNR^aSO_2NR^aR^{a1}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$, or —$(CR^aR^{a1})_r$-5–14 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

each $R^{c1}$ is, independently at each occurrence, H, $C_{1-4}$ alkyl, $OR^a$, Cl, F, Br, I, =O, $CF_3$, CN, $NO_2$, $C(O)R^a$, —$C(O)OR^a$, —$C(O)NR^aR^a$, or —$S(O)_pR^a$;

each $R^d$ is, independently at each occurrence, $C_{1-6}$ alkyl, $OR^a$, Cl, F, Br, I, =O, CN, $NO_2$, $NR^aR^{a1}$, $C(O)R^a$, —$C(O)OR^a$, —$(O)NR^aR^{a1}$, —$C(S)NR^aR^{a1}$, —$NR^aC(O)NR^aR^{a1}$, —$OC(O)NR^aR^{a1}$, —$NR^aC(O)OR^a$, —$S(O)_2NR^aR^{a1}$, —$NR^aS(O)_2R^{a3}$, —$NR^aS(O)_2NR^aR^{a1}$, —$OS(O)_2NR^aR^{a1}$, —$S(O)_pR^{a3}$, $CF_3$, $CF_2CF_3$, $C_{3-10}$ carbocycle, or a 5–14 membered heterocycle consisting of carbon atoms and 1–4 heteroatoms selected from the group consisting of N, O, and $S(O)_p$;

each $R^e$ is, independently at each occurrence, H, $C_{1-6}$ alkyl, $C_{1-6}$ alkoxy, phenoxy, benzoxy, $C_{3-10}$ carbocycle substituted with 0–2 $R^{c1}$, or a 5–10 membered heterocycle consisting of carbon atoms and 1–4 heteroatoms selected from the group consisting of N, O, and $S(O)_p$, and substituted with 0–2 $R^{c1}$;

m is 0, 1, 2 or 3;

n is 0, 1, 2, or 3;

each p is, independently at each occurrence, 0, 1, or 2;

each r is, independently at each occurrence, 0, 1, 2, 3, or 4;

each s is, independently at each occurrence, 0, 1, 2, 3, or 4; and each t is, independently at each occurrence, 2, 3, or 4.

In a second aspect, the present invention includes compounds of Formula (I) or a stereoisomer or pharmaceutically acceptable salt or solvate thereof, wherein:

$R^1$ is Q, F, Cl, Br, I, CN, $NO_2$, —$CF_2CF_3$, —$NR^7R^8$, $C_{1-4}$ haloalkyl, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$—Q, —$(CR^aR^{a1})_tNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_sS(CR^aR^{a1})_s$—Q, —$(CR^aR^{a1})_sS(O)(CR^aR^{a1})_s$—Q, —$(CR^aR^{a1})_sS(O)_2(CR^aR^{a1})_s$—Q, —$(CR^aR^{a1})_tSO_2NR^a(CR^aR^{a1})_s$—Q, or —$(CR^aR^{a1})_tNR^aSO_2(CR^aR^{a1})_s$—Q;

$R^5$ is Q, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$—Q, —$(CR^aR^{a1})_rNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_sS(CR^aR^{a1})_s$—Q, —$(CR^aR^{a1})_sS(O)(CR^aR^{a1})_s$—Q, —$(CR^aR^{a1})_rS(O)_2(CR^aR^{a1})_s$—Q, —$(CR^aR^{a1})_rSO_2NR^a(CR^aR^{a1})_s$—Q, or —$(CR^aR^{a1})_rN-R^aSO_2(CR^aR^{a1})_s$—Q;

$R^6$ is H, —$C_{1-6}$ alkylene-Q, —$C_{2-6}$ alkenylene-Q, or —$C_{2-6}$ alkynylene-Q;

each $R^9$ is, independently at each occurrence, H, —$(CR^aR^{a1})_rNR^aR^{a1}$, —$(CR^aR^{a1})_rC(O)NR_aOH$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rNR^aC(O)NR^aR^{a1}$, —$(CR^aR^{a1})_rS(O)R^{a3}$, —$(CR^aR^{a1})_rS(O)R^{a3}$, —$(CR^aR^{a1})_rS(O)_2R^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$; or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

each $R^{10}$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rNR^aC(O)NR^aR^{a1}$, —$(CR^aR^{a1})_rS(O)R^{a3}$, —$(CR^aR^{a1})_rS(O)R^{a3}$, —$(CR^aR^{a1})_rS(O)_2R^{a3}$, —$(CR^aR^{a1})_rSO_2NR^aR^{a1}$, —$(CR^aR^{a1})_rNR^aSO_2R^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —$(CR^aR^{a1})_r$—$C_{3-10}$ carbocycle substituted with 0–2 $R^{c1}$; or —$(CR^aR^{a1})_r$-5–10 membered heterocycle consisting of carbon atoms and 1–4 heteroatoms selected from the group consisting of N, O, and $S(O)_p$, and substituted with 0–2 $R^{c1}$;

each Q is, independently at each occurrence, H, $CF_3$, —$CH_2F$, —$CHF_2$, $C_{1-6}$ alkyl, a $C_{3-10}$ carbocycle substituted with 0–5 $R^d$, or a 5–10 membered heterocycle consisting of carbon atoms and 1–4 heteroatoms selected from the group consisting of $NR^9$, O, and $S(O)_p$, and substituted with 0–5 $R^d$;

each $Q^1$ is, independently at each occurrence, $C_{1-6}$ alkyl, a $C_{3-10}$ carbocycle substituted with 0–5 $R^d$, or a 5–12 membered heterocycle consisting of carbon atoms and 1–4 heteroatoms selected from the group consisting of $NR^9$, O, and $S(O)_p$, and substituted with 0–5 $R^d$;

$Z^0$ is aryl or a 5–6 membered heteroaryl consisting of carbon atoms and 0–3 ring heteroatoms selected from O, N, $NR^9$, and S, and substituted with 0–3 $R^{10}$; and the aryl or heteroaryl is optionally fused to a 5–6 membered carbocycle or heterocycle consisting of carbon atoms and 0–2 ring heteroatoms selected from O, N, $NR^9$, and $S(O)_p$, and 0–2 double bonds, and substituted with 0–3 $R^{10}$;

W is $(CR^aR^{a1})_m$, $C_{2-3}$ alkenylene, or $C_{2-3}$ alkynylene;

U is O, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$;

X is a bond or $C_{1-3}$ alkylene;

Y is a bond, O, $NR^{a1}$, $S(O)_p$, or C(O);

alternatively, $Z^0$ is absent, and W—U—X—Y forms $S(O)_p$;

Z is a $C_{3-8}$ cycloalkyl substituted with 0–5 $R^b$, a $C_{3-8}$ cycloalkenyl substituted with 0–5 $R^b$, phenyl substituted with 0–5 $R^b$, naphthyl substituted with 0–5 $R^b$ or a 5–14 membered heterocycle consisting of carbon atoms and 1–4 heteroatoms selected from the group consisting of N, O, and $S(O)_p$ and substituted with 0–5 $R^b$;

$U^a$ is a bond, O, $NR^{a1}$, C(O), $CR^a(OH)$, C(O)O, $C(O)NR^{a1}$, $NR^{a1}C(O)$, $S(O)_p$, $S(O)_pNR^{a1}$, or $NR^{a1}S(O)_p$;

$X^a$ is a bond, $C_{1-4}$ alkylene, $C_{2-4}$ alkenylene, or $C_{2-4}$ alkynylene;

$Y^a$ is a bond, O, or $NR^{a1}$;

$Z^a$ is a $C_{6-13}$ carbocycle substituted with 0–5 $R^c$, or a 5–14 membered heterocycle consisting of carbon atoms and 1–4 heteroatoms selected from the group consisting of N, O, and $S(O)_p$ and substituted with 0–5 $R^c$;

provided that U, Y, Z, $U^a$, $Y^a$, and $Z^a$ do not combine to form a N—N, N—O, O—N, O—O, $S(O)_p$—O, O—$S(O)_p$ or $S(O)_p$—$S(O)_p$ group;

each $R^c$ is, independently at each occurrence, H, Cl, F, Br, I, =O, CN, $NO_2$, $CF_3$, $CF_2CF_3$, $CH_2F$, $CHF_2$, —$(CR^aR^{a1})_r$$OR^a$, —$(CR^aR^{a1})_rNR^aR^{a1}$, —$(CR^aR^{a1})_rC(O)NR^aOH$, —$(CR^aR^{a1})_rC(O)R^{a1}$, —$(CR^aR^{a1})_rC(O)OR^{a1}$, —$(CR^aR^{a1})_rC(O)R^{a1}$, —$(CR^aR^{a1})_rNR^aC(O)R^{a1}$, —$(CR^aR^{a1})_r$$S(O)_pR^{a3}$, —$(CR^aR^{a1})_rSO_2NR^aR^{a1}$, —$(CR^aR^{a1})_r$$NR^aSO_2R^{a3}$, $C_{1-6}$ alkyl substituted with 0–1 $R^{c1}$, $C_{2-6}$ alkenyl substituted with 0–1 $R^{c1}$, $C_{2-6}$ alkynyl substituted with 0–1 $R^{c1}$, —$(CH_2)_r$—$C_{3-6}$ carbocycle substituted with 0–2 $R^{c1}$, or —$(CH_2)_r$-5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to the same carbon atom, they form a 3–8 membered carbocyclic or heterocyclic spiro ring C substituted with 0–2 $R^{c1}$ and consisting of carbon atoms, 0–4 ring heteroatoms selected from O, N, and $S(O)_p$, and 0–2 double bonds, provided that ring C contains other than a S—S, O—O, or S—O bond;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds; and each $R^d$ is, independently at each occurrence, $C_{1-6}$ alkyl, $OR^a$, Cl, F, Br, I, =O, CN, $NO_2$, $NR^aR^{a1}$, $C(O)R^a$, —$C(O)OR^a$, —$C(O)NR^aR^{a1}$, —$S(O)_2NR^aR^{a1}$, —$NR^aS(O)_2R^{a3}$, —$S(O)^yR^{a3}$, $CF_3$, $C_{3-6}$ carbocycle, or a 5–6 membered heterocycle consisting of carbon atoms and 1–4 heteroatoms selected from the group consisting of N, O, and $S(O)_p$.

In a third aspect, the present invention includes compounds of Formula (I) or a stereoisomer or pharmaceutically acceptable salt or solvate thereof, wherein:

$R^1$ is Q, F, Cl, CN, —$NR^7R^8$, $C_{1-4}$ haloalkyl, —$C_{1-4}$ alkylene-Q, —$C_{2-4}$ alkenylene-Q, —$C_{2-4}$ alkynylene-Q, —$(CR^aR^{a1})_tO(CR^aR^{a1})_s$—Q, —$(CR^aR^{a1})_tNR^a(CR^aR^{a1})_s$—Q, $(CR^aR^{a1})_rC(O)(CR^aR^{a1})_s$—Q, —$(CR^aR^{a1})_rC(O)$$O(CR^aR^{a1})_s$—Q, —$(CR^aR^{a1})_rC(O)NR^aR^{a1}$, —$(CR^aR^{a1})_rC(O)NR_a(CR^aR_{a1})_s$—Q, —$(CR_aR_{a1})_rS(CR^aR^{a1})_s$—Q, —$(CR^aR^{a1})_rS(O)(CR^aR^{a1})_s$—Q, —$(CR^aR^{a1})_rS(O)_2$$(CR^aR^{a1})_s$—Q, —$(CR^aR^{a1})_rSO_2NR^a(CR^aR^{a1})_s$—Q, or —$(CR^aR^{a1})_rNR^aSO_2(CR^aR^{a1})_s$—Q;

$R^2$ is H or $C_{1-4}$ alkyl;

$R^3$ is H or $C_{1-4}$ alkyl;

$R^5$ is Q, $C_{1-4}$ alkyl, $C_{2-4}$ alkenyl, $C_{2-4}$ alkynyl, —$(CH_2)_t$$O(CH_2)_s$—Q, —$(CH_2)_rNR^a(CH_2)_s$—Q, —$(CH_2)_rC(O)$$(CH_2)_s$—Q, —$(CH_2)_rC(O)O(CH_2)_s$—Q, —$(CH_2)_rOC(O)$$(CH_2)_s$—Q, —$(CH_2)_rC(O)NR^aR^{a1}$, —$(CH_2)_rC(O)NR^a$$(CH_2)_s$—Q, —$(CH_2)_rNR^aC(O)(CH_2)_s$—Q, —$(CH_2)_rS$$(CH_2)_s$—Q, —$(CH_2)_rS(O)(CH_2)_s$—Q, —$(CH_2)_rS(O)_2$$(CH_2)_s$—Q, —$(CH_2)_rSO_2NR^a(CH_2)_s$—Q, or —$(CH_2)_r$$NR^aSO_2(CH_2)_s$—Q;

$R^6$ is H, —$C_{1-4}$ alkyl, $C_{2-4}$ alkenyl, or $C_{2-4}$ alkynyl;

$R^7$ is H, $C_{1-4}$ alkyl, $C_{2-4}$ alkenyl, $C_{2-4}$ alkynyl, —$(CR^aR^{a1})_rC(O)(CR^aR^{a1})_s$—$Q^1$, —$(CR^aR^{a1})_rC(O)O(CR^aR^{a1})_s$—$Q^1$, —$(CR^aR^{a1})_rC(O)O(CR^aR^{a1})_tOC(O)$—$Q^1$, —$(CR^aR^{a1})_rC(O)NH(CR^aR^{a1})_s$—$Q^1$, or —$(CR^aR^{a1})_rS(O)_2)(CR_aR_{a1})_s$—$Q^1$;

$R^8$ is H, $C_{1-4}$ alkyl, or —$(CH_2)_n$-phenyl;

each $R^9$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)R^{a3}$, —$(CR^aR^{a1})_rS(O)R^{a3}$, —$(CR^aR^{a1})_rS(O)_2R^{a3}$, —$(CR^aR^{a1})SO_2NR^aR^{a1}$, —$(CR^aR^{a1})_t$$NR^aSO_2R^{a3}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, —$(CH_2)_r$—$C_{3-10}$ carbocycle substituted with 0–2 $R^{c1}$; or —$(CH_2)_r$-5–10 membered heterocycle consisting of carbon atoms and 1–4 heteroatoms selected from the group consisting of N, O, and $S(O)_p$, and substituted with 0–2 $R^{c1}$;

each $R^{10}$ is, independently at each occurrence, H, —$(CR^aR^{a1})_rNR^aR^{a1}$, —$(CR^aR^{a1})_rC(O)NR^aOH$, —$(CR^aR^{a1})_rC(O)(CR^aR^{a1})_sR^e$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)R^{a3}$, —$(CR^aR^{a1})_rS(O)R^{a3}$, —$(CR^aR^{a1})_rS(O)_2R^{a3}$, —$(CR^aR^{a1})_rSO_2NR^aR^{a1}$, —$(CR^aR^{a1})_r$$NR^aSO_2R^{a3}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, —$(CH_2)_r$—$C_{3-10}$ carbocycle substituted with 0–2 $R^{c1}$; or —$(CH_2)_r$-5–10 membered heterocycle consisting of carbon atoms and 1–4 heteroatoms selected from the group consisting of N, O, and $S(O)_p$, and substituted with 0–2 $R^{c1}$;

$Z^0$ is phenyl substituted with 0–3 $R^{10}$, or a 5–6 membered heteroaryl substituted with 0–3 $R^{10}$ and selected from: oxazolyl, isoxazolyl, thiazolyl, isothiazolyl, imidazolyl, pyrrolyl, furanyl, thienyl, pyridyl, pyrimidinyl, pyridazinyl, pyrazinyl, or pyrazolyl;

W is $(CH_2)_m$;

U is O, C(O), $CR^a(OH)$, $C(O)NR^{a1}$, $NR^{a1}C(O)$, $S(O)_p$, $S(O)_pNR^{a1}$, or $NR^{a1}S(O)_p$;

X is a bond, or methylene or ethylene;

Y is a bond, O, $NR^{a1}$, $S(O)_p$, or C(O);

alternatively, $Z^O$ is absent, and W—U—X=Y forms $S(O)_p$;

$U^d$ is a bond, O, $NR^{a1}$, C(O), C(O)$NR^{a1}$, $NR^{a1}$C(O), $S(O)_p$, $S(O)_p NR^{a1}$, or $NR^{a1}S(O)_p$;

each $R^c$ is, independently at each occurrence, H, Cl, F, Br, I, =O, CN, $NO_2$, $CF_3$, $CH_2F$, $CHF_2$, —$(CR^aR^{a1})_rOR^a$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, —$(CH_2)_r$—$C_{3-6}$ cycloalkyl substituted with 0–1 $R^{c1}$, phenyl substituted with 0–2 $R^{c1}$, or —$(CH_2)_r$-5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

each $R^d$ is, independently at each occurrence, $C_{1-6}$ alkyl, $OR^a$, Cl, F, Br, I, =O, $NR^aR^{a1}$, $C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, $CF_3$, or phenyl;

m is 0, 1, or 2;

n is 0, 1, or 2;

each r is, independently at each occurrence, 0, 1, 2, or 3;

each s is, independently at each occurrence, 0, 1, 2, or 3; and each t is, independently at each occurrence, 2, or 3.

In a fourth aspect, the present invention includes compounds of Formula (I) or a stereoisomer or pharmaceutically acceptable salt or solvate thereof, wherein:

A is O;

$R^1$ is Q, F, Cl, CN, —$NR^7R^8$, $C_{1-4}$ haloalkyl, -$C_{1-4}$ alkylene-Q, —$C_{2-4}$ alkenylene-Q, —$C_{2-4}$ alkynylene-Q, —$(CH_2)_rO(CH_2)_s$—Q, —$(CH_2)_rNR^a(CH_2)_s$—Q, —$(CH_2)_rC(O)(CH_2)_s$—Q, —$(CH_2)_rC(O)O(CH_2)_s$—Q, —$(CH_2)_rC(O)$ $NR^aR^{a1}$, —$(CH_2)_rC(O)NR^a(CH_2)_s$—Q, —$(CH_2)_rS(CH_2)_s$—Q, —$(CH_2)_rS(O)(CH_2)_s$—Q, —$(CH_2)_rS(O)_2(CH_2)_s$—Q, —$(CH_2)_rSO_2NR^a(CH_2)_s$—Q, or —$(CH_2)_tNR^aSO_2(CH_2)_s$—Q;

$R^5$ is H, $C_{1-4}$ alkyl, $C_{2-4}$ alkenyl, or $C_{2-4}$ alkynyl;

$R^7$ is H, $C_{1-4}$ alkyl, or —$(CH_2)_n$-phenyl;

$R^8$ is H, $C_{1-4}$ alkyl, or —$(CH_2)_n$-phenyl;

each $R^9$ is, independently at each occurrence, H, —$(CH_2)_t$ $NR^aR^{a1}$, —$(CH_2)_rC(O)(CH_2)_sR^e$, —$(CH_2)_rC(O)OR^{a1}$, —$(CH_2)_rC(O)NR^aR^{a1}$, —$(CH_2)_rNR^aC(O)R^{a1}$, —$(CH_2)_tS(O)R^{a3}$, —$(CH_2)_rS(O)R^{a3}$, —$(CH_2)_rS(O)_2R^{a3}$, —$(CH_2)_rSO_2NR^aR^{a1}$, —$(CH_2)_rNR^aSO_2R^{a3}$, $C_{1-4}$ alkyl, or —$(CH_2)_n$-phenyl;

each $R^{10}$ is, independently at each occurrence, H, —$(CH_2)_rNR^aR^{a1}$, —$(CH_2)_rC(O)(CH_2)_sR^e$, —$(CH_2)_rC(O)OR^{a1}$, —$(CH_2)_rC(O)NR^aR^{a1}$, —$(CH_2)_rNR^aC(O)R^{a1}$, —$(CH_2)_rS(O)R^{a3}$, —$(CH_2)_rS(O)R^{a3}$, —$(CH_2)_rS(O)_2R^{a3}$, —$(CH_2)_rSO_2NR^aR^{a1}$, —$(CH_2)_rNR^aSO_2R^{a3}$, $C_{1-4}$ alkyl, or —$(CH_2)_n$-phenyl;

$Z^O$ is phenyl substituted with 0–2 $R^{10}$, or pyridyl substituted with 0–2 $R^{10}$;

alternatively, $Z^O$ is absent, and W—U—X—Y forms $S(O)_p$;

U is O, C(O), CH(OH), C(O)NH, NHC(O), $S(O)_p$, $S(O)_p$ NH, or NHS(O)$_p$;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

each $R^c$ is, independently at each occurrence, H, Cl, F, Br, =O, $CF_3$, $CH_2F$, $CHF_2$, —$(CR^aR^{a1})_rOR^a$, —$(CR^aR^{a1})_rNR^aR^{a1}$, —$(CR^aR^{a1})_rC(O)R^{a1}$, —$(CR^aR^{a1})_rC(O)OR^{a1}$, —$(CR^aR^{a1})_rC(O)NR^aR^{a1}$, —$(CR^aR^{a1})_rNR^aC(O)R^{a1}$, —$(CR^aR^{a1})_rS(O)_pR^{a3}$, —$(CR^aR^{a1})_rSO_2NR^aR^{a1}$, —$(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or a 5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds; and each $R^d$ is, independently at each occurrence, $C_{1-6}$ alkyl, $OR^a$, Cl, F, Br, I, =O, $NR^aR^{a1}$, $C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, $CF_3$, or phenyl.

In a fifth aspect, the present invention includes compounds of Formula (I) or a stereoisomer or pharmaceutically acceptable salt or solvate thereof, wherein:

A is O;

L is a bond, CO or $CH_2$;

$R^1$ is H, $C_{1-4}$ haloalkyl, $C_{1-4}$ alkyl, or —$C(O)O(CH_2)_s$—H;

$Z^O$ is phenyl;

alternatively, $Z^O$ is absent, and W—U—X—Y forms $S(O)_p$;

Z is phenyl substituted with 0–2 $R^b$;

$Z^a$ is phenyl substituted with 0–3 $R^c$, naphthyl substituted with 0–3 $R^c$, or a heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

each $R^b$ is, independently at each occurrence, $C_{1-6}$ alkyl, —$OR^a$, Cl, F, Br, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, or $CF_3$;

each $R^c$ is, independently at each occurrence, H, $C_{1-6}$ alkyl, $C_{2-6}$ alkenyl, $C_{2-6}$ alkynyl, Cl, F, Br, =O, $CF_3$, —$(CH_2)_rOR^a$, —$(CH_2)_rNR^aR^{a1}$, —$(CH_2)_rC(O)R^{a1}$, —$(CH_2)_rC(O)OR^{a1}$, —$(CH_2)_rC(O)NR^aR^{a1}$, —$(CH_2)_rNR^aC(O)R^{a1}$, —$(CH_2)_rS(O)_pR^{a3}$, —$(CH_2)_rSO_2NR^aR^{a1}$, or —$(CH_2)_rNR^aSO_2R^{a3}$;

alternatively, when two $R^c$ groups are attached to adjacent carbon atoms, together with the carbon atoms to which they are attached they form a 5–6 membered carbocyclic or heterocyclic ring consisting of: carbon atoms and 0–1 heteroatoms selected from the group consisting of N, O, and $S(O)_p$; and each $R^e$ is, independently at each occurrence, H, $C_{1-6}$ alkyl, $C_{1-6}$ alkoxy, phenoxy, benzoxy, phenyl substituted with 0–1 $R^{c1}$, or a 5–6 membered heterocycle consisting of carbon atoms and 1–4 heteroatoms selected from the group consisting of N, O, and $S(O)_p$, and substituted with 0–1 $R^{c1}$.

In a sixth aspect, the present invention provides a compound selected from Examples 1–7 or a stereoisomer or a pharmaceutically acceptable salt or solvate thereof.

In some embodiments according to the first aspect, the present invention includes compounds of Formula (I) where A is O. In other embodiments, A is S.

In some embodiments according to the first aspect, the present invention includes compounds of Formula (I) where L is a bond, CO, or $CR^5R^6$. In other embodiments, L is a bond, CO or $CH_2$. In other embodiments, L is CO or $CH_2$.

In some embodiments according to the first aspect, the present invention includes compounds of Formula (I) where $R^1$ is Q, F, Cl, Br, I, CN, $NO_2$, —$CF_2CF_3$, —$NR^7R^8$, $C_{1-4}$ haloalkyl, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$—Q, —$(CR^aR^{a1})_tNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_rS(CR^aR^{a1})_s$—Q, —$(CR^aR^{a1})_rS(O)(CR^aR^{a1})_s$—Q, —$(CR^aR^{a1})_rS(O)_2(CR^aR^{a1})_s$—Q, —$(CR^aR^{a1})_tSO_2NR^a(CR^aR^{a1})_s$—Q, or —$(CR^aR^{a1})_tNR^aSO_2(CR^aR^{a1})_s$—Q. In other embodiments, $R^1$ is Q, F, Cl, CN, —$NR^7R^8$, $C_{1-4}$ haloalkyl, —$C_{1-4}$ alkylene-Q, —$C_{2-4}$ alkenylene-Q, —$C_{2-4}$ alkynylene-Q, —$(CR^aR^{a1})_tO(CR^aR^{a1})_s$—Q, —$(CR^aR^{a1})_tNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rS(CR^aR^{a1})_s$—Q, —$(CR^aR^{a1})_rS(O)(CR^aR^{a1})_s$—Q, —$(CR_aR^{a1})_rS(O)_2(CR^aR^{a1})_s$—Q, —$(CR^aR^{a1})_rSO_2NR^a(CR^aR^{a1})_s$—Q, or —$(CR^aR^{a1})_tNR^aSO_2(CR^aR^{a1})_s$—Q. In other embodiments, $R^1$ is Q, F, Cl, CN, —$NR^7R^8$, $C_{1-4}$ haloalkyl, —$C_{1-4}$ alkylene-Q, —$C_{2-4}$ alkenylene-Q, —$C_{2-4}$ alkynylene-Q, —$(CH_2)_tO(CH_2)_s$—Q, —$(CH_2)_tNR^a(CH_2)_s$—Q, —$(CH_2)_rC(O)(CH_2)_s$—Q, —$(CH_2)_rC(O)O(CH_2)_s$—Q, —$(CH_2)_rC(O)NR^aR^{a1}$, —$(CH_2)_rC(O)NR^a(CH_2)_s$—Q, —$(CH_2)_rS(CH_2)_s$—Q, —$(CH_2)_rS(O)(CH_2)_s$—Q, —$(CH_2)_rS(O)_2(CH_2)_s$—Q, —$(CH_2)_rSO_2NR^a(CH_2)_s$—Q, or —$(CH_2)_tNR^aSO_2(CH_2)_s$—Q. In other embodiments, $R^1$ is Q, $C_{1-4}$ haloalkyl, —$C_{1-4}$ alkylene-Q, —$C_{2-4}$ alkenylene-Q, or —$C_{2-4}$ alkynylene-Q. In other embodiments, $R^1$ is H, $C_{1-4}$ haloalkyl, $C_{1-4}$ alkyl, or —$C(O)O(CH_2)_s$—H.

In some embodiments according to the first aspect, the present invention includes compounds of Formula (I) where $R^2$ is H or $C_{1-4}$ alkyl. In other embodiments, $R^2$ is H or methyl.

In some embodiments according to the first aspect, the present invention includes compounds of Formula (I) where $R^3$ is H or $C_{1-4}$ alkyl. In other embodiments, $R^3$ is H or methyl.

In some embodiments according to the first aspect, the present invention includes compounds of Formula (I) where $R^5$ is Q, —$C_{1-6}$ alkylene-Q, —$C_{2-6}$ alkenylene-Q, —$C_{2-6}$ alkynylene-Q, —$(CR^aR^{a1})_tO(CR^aR^{a1})_s$—Q, —$(CR^aR^{a1})_tNR^a(CR^aR^{a1})_s$—Q, —$(CR^aR^{a1})_rC(O)(CR^aR^{a1})_s$—Q, —$(CR^aR^{a1})_rC(O)O(CR^aR^{a1})_s$—Q, —$(CR^aR^{a1})_rOC(O)(CR^aR^{a1})_s$—Q, —$(CR^aR^{a1})_rC(O)NR^aR^{a1}$, —$(CR^aR^{a1})_rC(O)NR^a(CR^aR^{a1})_s$—Q, —$(CR^aR^{a1})_rNR^aC(O)(CR^aR^{a1})_s$—Q, —$(CR^aR^{a1})_rS(CR^aR^{a1})_s$—Q, —$(CR^aR^{a1})_rS(O)(CR^aR^{a1})_s$—Q, —$(CR^aR^{a1})_rS(O)_2(CR^aR^{a1})_s$—Q, —$(CR^aR^{a1})_rSO_2NR^a(CR^aR^{a1})_s$—Q, or —$(CR^aR^{a1})_tNR^aSO_2(CR^aR^{a1})_s$—Q. In other embodiments, $R^5$ is Q, $C_{1-4}$ alkyl, $C_{2-4}$ alkenyl, $C_{2-4}$ alkynyl, —$(CH_2)_tO(CH_2)_s$—Q, —$(CH_2)_tNR^a(CH_2)_s$—Q, —$(CH_2)_rC(O)(CH_2)_s$—Q, —$(CH_2)_rC(O)O(CH_2)_s$—Q, —$(CH_2)_rOC(O)(CH_2)_s$—Q, —$(CH_2)_rC(O)NR^aR^{a1}$, —$(CH_2)_rC(O)NR^a(CH_2)_s$—Q, —$(CH_2)_rNR^aC(O)(CH_2)_s$—Q, —$(CH_2)_rS(CH_2)_s$—Q, —$(CH_2)_rS(O)(CH_2)_s$—Q, —$(CH_2)_rS(O)_2(CH_2)_s$—Q, —$(CH_2)_rSO_2NR^a(CH_2)_s$—Q, or —$(CH_2)_tNR^aSO_2(CH_2)_s$—Q. In other embodiments, $R^5$ is H, $C_{1-4}$ alkyl, $C_{2-4}$ alkenyl, or $C_{2-4}$ alkynyl.

In some embodiments according to the first aspect, the present invention includes compounds of Formula (I) where $R^6$ is H, —$C_{1-6}$ alkylene-Q, —$C_{2-6}$ alkenylene-Q, or —$C_{2-6}$ alkynylene-Q. In other embodiments, $R^6$ is H, —$C_{1-4}$ alkyl, $C_{2-4}$ alkenyl, or $C_{2-4}$ alkynyl.

In some embodiments according to the first aspect, the present invention includes compounds of Formula (I) where $Z^0$ is phenyl substituted with 0–3 $R^{10}$, or a 5–6 membered heteroaryl substituted with 0–3 $R^{10}$ and selected from: oxazolyl, isoxazolyl, thiazolyl, isothiazolyl, imidazolyl, pyrrolyl, furanyl, thienyl, pyridyl, pyrimidinyl, pyridazinyl, pyrazinyl, or pyrazolyl. In other embodiments, $Z^0$ is phenyl substituted with 0–2 $R^{10}$, or pyridyl substituted with 0–2 $R^{10}$. In other embodiments, $Z^0$ is phenyl.

In some embodiments according to the first aspect, the present invention includes compounds of Formula (I) where W is $(CR^aR^{a1})_m$, $C_{2-3}$ alkenylene, or $C_{2-3}$ alkynylene. In other embodiments, W is $(CH_2)_m$.

In some embodiments according to the first aspect, the present invention includes compounds of Formula (I) where U is O, C(O), $CR^a(OH)$, C(O)O, OC(O), $C(O)NR^{a1}$, $NR^{a1}C(O)$, $S(O)_p$, $S(O)_pNR^{a1}$, or $NR^{a1}S(O)_p$. In other embodiments, U is O, C(O), $CR^a(OH)$, $C(O)NR^{a1}$, $NR^{a1}C(O)$, $S(O)_p$, $S(O)_pNR^{a1}$, or $NR^{a1}S(O)_p$. In other embodiments, U is O, C(O), CH(OH), C(O)NH, NHC(O), $S(O)_p$, $S(O)_pNH$, or $NHS(O)_p$. In other embodiments, U is O, C(O), CH(OH), C(O)NH, NHC(O), $S(O)_p$, $S(O)_pNH$, or $NHS(O)_p$. In other embodiments, U is O, C(O), C(O)NH, NHC(O), $S(O)_p$, $S(O)_pNH$, or $NHS(O)_p$.

In some embodiments according to the first aspect, the present invention includes compounds of Formula (I) where X is a bond or $C_{1-3}$ alkylene. In other embodiments, X is a bond, or methylene or ethylene.

In some embodiments according to the first aspect, the present invention includes compounds of Formula (I) where $U^a$ is a bond, O, $NR^{a1}$, C(O), $CR^a$(OH), C(O)O, C(O)$NR^{a1}$, $NR^{a1}$C(O), S(O)$_p$, S(O)$_p$$NR^{a1}$, or $NR^{a1}$S(O)$_p$. In other embodiments, $U^a$ is a bond, O, $NR^{a1}$, C(O), C(O)$NR^{a1}$, $NR^{a1}$C(O), S(O)$_p$, S(O)$_p$$NR^{a1}$, or $NR_{a1}$S(O)$_p$. In other embodiments, $U^a$ is O, C(O), CH(OH), C(O)NH, NHC(O), S(O)$_p$, S(O)$_p$NH, or NHS(O)$_p$. In other embodiments, $U^a$ is O, C(O), CH(OH), C(O)NH, NHC(O), S(O)$_p$, S(O)$_p$NH, or NHS(O)$_p$. In other embodiments, $U^a$ is O, C(O), C(O)NH, NHC(O), S(O)$_p$, S(O)$_p$NH, or NHS(O)$_p$.

In some embodiments according to the first aspect, the present invention includes compounds of Formula (I) where $X^a$ is a bond, $C_{1-4}$ alkylene, $C_{2-4}$ alkenylene, or $C_{2-4}$ alkynylene. In other embodiments, $X^a$ is a bond or $C_{1-3}$ alkylene. In other embodiments, $X^a$ is a bond, or methylene or ethylene.

In some embodiments according to the first aspect, the present invention includes compounds of Formula (I) where Z is a $C_{3-8}$ cycloalkyl substituted with 0–5 $R^b$, a $C_{3-8}$ cycloalkenyl substituted with 0–5 $R^b$, phenyl substituted with 0–5 $R^b$, naphthyl substituted with 0–5 $R^b$ or a 5–14 membered heterocycle consisting of carbon atoms and 1–4 heteroatoms selected from the group consisting of N, O, and S(O)$_p$ and substituted with 0–5 $R^b$. In other embodiments, Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl. In other embodiments, Z is phenyl substituted with 0–2 $R^b$.

In some embodiments according to the first aspect, the present invention includes compounds of Formula (I) where $Z^a$ is a $C_{6-13}$ carbocycle substituted with 0–5 $R^c$, or a 5–14 membered heterocycle consisting of carbon atoms and 1–4 heteroatoms selected from the group consisting of N, O, and S(O)$_p$ and substituted with 0–5 $R^c$. In other embodiments, $Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl. In other embodiments, $Z^a$ is phenyl substituted with 0–3 $R^c$, naphthyl substituted with 0–3 $R^c$, or a heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl.

In some embodiments according to the first aspect, the present invention includes compounds of Formula (I) where each $R^9$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_t$NR$^a$C(O)R$^{a1}$, —(CR$^a$R$^{a1}$)$_t$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)SO$_2$NR$^a$R$^{a1}$, —(CR$^a$R$^{a1}$)$_t$NR$^a$SO$_2$R$^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —(CR$^a$R$^{a1}$)$_r$—$C_{3-10}$ carbocycle substituted with 0–2 $R^{c1}$; or (CR$^a$R$^{a1}$)$_r$-5–10 membered heterocycle consisting of carbon atoms and 1–4 heteroatoms selected from the group consisting of N, O, and S(O)$_p$, and substituted with 0–2 $R^{c1}$. In other embodiments, each $R^9$ is, independently at each occurrence, H, —(CR$^a$R$^{a1}$)$_t$NR$^a$R$_{a1}$, (CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_t$NR$^a$C(O)R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)SO$_2$NR$^a$R$^{a1}$, —(CR$^a$R$^{a1}$)$_t$NR$_a$SO$_2$R$^{a3}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, —(CH$_2$)$_r$—$C_{3-10}$ carbocycle substituted with 0–2 $R^{c1}$; or —(CH$_2$)$_r$-5–10 membered heterocycle consisting of carbon atoms and 1–4 heteroatoms selected from the group consisting of N, O, and S(O)$_p$, and substituted with 0–2 $R^{c1}$. In other embodiments, each $R^9$ is, independently at each occurrence, H, —(CH$_2$)$_t$NR$^a$R$^{a1}$, —(CH$_2$)$_r$C(O)(CH$_2$)$_s$R$^e$, —(CH$_2$)$_r$C(O)OR$^{a1}$, —(CH$_2$)$_r$C(O)NR$^a$R$^{a1}$, —(CH$_2$)$_t$NR$^a$C(O)R$^{a1}$, —(CH$_2$)$_r$S(O)R$^{a3}$, —(CH$_2$)$_r$S(O)R$^{a3}$, —(CH$_2$)$_r$S(O)$_2$R$^{a3}$, —(CH$_2$)SO$_2$NR$^a$R$^{a1}$, —(CH$_2$)$_t$NR$^a$SO$_2$R$^{a3}$, $C_{1-4}$ alkyl, or —(CH$_2$)$_n$-phenyl.

In some embodiments according to the first aspect, the present invention includes compounds of Formula (I) where each $R^{10}$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_t$NR$^a$C(O)R$^{a1}$, —(CR$^a$R$^{a1}$)$_t$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_t$NR$^a$SO$_2$R$^{a3}$, $C_{1-6}$ alkyl substituted with 0–2 $R^{c1}$, $C_{2-6}$ alkenyl substituted with 0–2 $R^{c1}$, $C_{2-6}$ alkynyl substituted with 0–2 $R^{c1}$, —(CR$^a$R$^{a1}$)$_r$—$C_{3-10}$ carbocycle substituted with 0–2 $R^{c1}$; or (CR$^a$R$^{a1}$)$_r$-5–10 membered heterocycle consisting of carbon atoms and 1–4 heteroatoms selected from the group consisting of N, O, and S(O)$_p$, and substituted with 0–2 $R^{c1}$. In other embodiments, each $R^{10}$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_t$NR$^a$C(O)R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, $C_{1-4}$ alkyl substituted with 0–1 $R^{c1}$, $C_{2-4}$ alkenyl substituted with 0–1 $R^{c1}$, $C_{2-4}$ alkynyl substituted with 0–1 $R^{c1}$, —(CH$_2$)$_r$—$C_{3-10}$ carbocycle substituted with 0–2 $R^{c1}$; or —(CH$_2$)$_r$-5–10 membered heterocycle consisting of carbon atoms and 1–4 heteroatoms selected from the group consisting of N, O, and S(O)$_p$, and substituted with 0–2 $R^{c1}$. In other embodiments, each $R^{10}$ is, independently at each occurrence, H, —(CH$_2$)$_t$NR$^a$R$^{a1}$, —(CH$_2$)$_r$C(O)(CH$_2$)$_s$R$^e$, —(CH$_2$)$_r$C(O)OR$^{a1}$, —(CH$_2$)$_r$C(O)NR$^a$R$^{a1}$, —(CH$_2$)$_t$NR$^a$C(O)R$^{a1}$, —(CH$_2$)$_r$S(O)R$^{a3}$, —(CH$_2$)$_r$S(O)R$^{a3}$, —(CH$_2$)$_r$ $S(O)_2R^{a3}$, $-(CH_2)_rSO_2NR^aR^{a1}$, $-(CH_2)_rNR^aSO_2R^{a3}$, $C_{1-4}$ alkyl, or $-(CH_2)_n$-phenyl.

In another embodiment, the present invention provides a novel pharmaceutical composition, comprising: a pharmaceutically acceptable carrier and a therapeutically effective amount of a compound of the present invention or a stereoisomer or a pharmaceutically acceptable salt or solvate thereof.

In another embodiment, the present invention provides a novel method for treating or preventing an inflammatory disorder, comprising: administering to a patient in need thereof a therapeutically effective amount of a compound of the present invention or a stereoisomer or a pharmaceutically acceptable salt or solvate thereof.

In another embodiment, the present invention provides a novel method of treating a condition or disease mediated by MMPs, TACE, aggrecanase, or a combination thereof in a mammal, comprising: administering to the mammal in need of such treatment a therapeutically effective amount of a compound of the present invention or a stereoisomer or a pharmaceutically acceptable salt or solvate thereof.

In another embodiment, the present invention provides a novel method comprising: administering a compound of the present invention or a stereoisomer or a pharmaceutically acceptable salt or solvate thereof, in an amount effective to treat a condition or disease mediated by MMPs, TACE, aggrecanase, or a combination thereof.

In another embodiment, the present invention provides a novel method of treating a disease or condition, wherein the disease or condition is selected from acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia, calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy, Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis, sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

In another embodiment, the present invention provides novel compounds of the present invention for use in therapy.

In another embodiment, the present invention provides the use of novel compounds of the present invention for the manufacture of a medicament for the treatment of a condition or disease mediated by MMPs, TACE, aggrecanase, or a combination thereof.

In another embodiment, the present invention provides a method for treating inflammatory disorders, comprising: administering, to a host in need of such treatment, a therapeutically effective amount of one of the compounds of the present invention, in combination with one or more additional anti-inflammatory agents selected from selective COX-2 inhibitors, interleukin-1 antagonists, dihydroorotate synthase inhibitors, p38 MAP kinase inhibitors, TNF-α inhibitors, TNF-α sequestration agents, and methotrexate.

In another embodiment, the present invention provides a medical device for implanting into a mammalian body wherein the medical device has a coating material comprising an amount of one of the compounds of the present invention or a stereoisomer or a pharmaceutically acceptable salt or solvate thereof, effective for reducing inflammation or restinosis.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or or a stereoisomer or a pharmaceutically acceptable salt or solvate thereof; and, (c) a package insert stating that the pharmaceutical composition can be used for the treatment of an inflammatory disorder.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a stereoisomer or a pharmaceutically acceptable salt or solvate thereof; and, (c) a package insert stating that the pharmaceutical composition can be used in combination with a second therapeutic agent to treat an inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$–$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$–$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_2$–$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_2$–$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2C_5$, and the like.

The term "alkoxy" or "alkyloxy" refers to an —O-alkyl group. "$C_1$–$C_6$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_1$–$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7- membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from the group consisting of N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, acridinyl, azocinyl, benzimidazolyl, benzofuranyl, benzothiophenyl, benzoxazolyl, benzthiazolyl, benztriazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, 1,1-dioxido-2,3-dihydro-4H-1,4-benzothiazin-4-yl, 1,1-dioxido-3,4-dihydro-2H-1-benzothiopyran-4-yl, and 3,4-dihydro-2H-chromen-4-yl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazolyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0–3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifying functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}C$ or by $^{14}C$; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa. "Therapeutically effective amount" is also intended to include an amount of the combination of compounds claimed that is effective to inhibit factor XIa. The combination of compounds is preferably a synergistic combination. Synergy, as described, for example, by Chou and Talalay, *Adv. Enzyme Regul.* 1984, 22:27–55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1999).

The optionally substituted 1,3-dihydroimidazol-3-ones and 1,3-dihydroimidazol-3-thiones of Formula I in the present invention can be synthesized using a variety of literature methods both in solution and on solid support by one skilled in the art of organic synthesis. Several literature precedented syntheses of these heterocycles are listed in Scheme 1. A common and efficient means of preparing compounds of Formula I is starting from halomethyl ketones and condensing with urea. As depicted in Scheme 1, entry (1) SN2 reaction of the urea nitrogen with a halomethyl ketone 1 yields ureidoketones 2 which are poised for dehydration, usually under acidic conditions to give the target heterocycle 3 (see Fevig et al *Bioorg Med Chem Lett,* 2001, 11, 641–645). Use of α-hydroxymethylketones entry (2) is also precedented to condense with urea or thiourea under acidic conditions to form imines which tautomerize to ureidoketone 6 and dehydrate to give the desired heterocycle 7 (see *Justus Liebegs Ann. Chem.* 1895, 284,13 and *J. Chem. Soc. Perkin Trans II,* 1981, 310–316).

Scheme 1. Heterocycle Synthetic Routes (1) 1,3-dihydroimidazol-2-ones from α-halomethyl-ketones (2) 1,3-dihydroimidazol-2-ones and 1,3-dihydroimidazol-2-thiones from α-hydroxymethyl-ketones

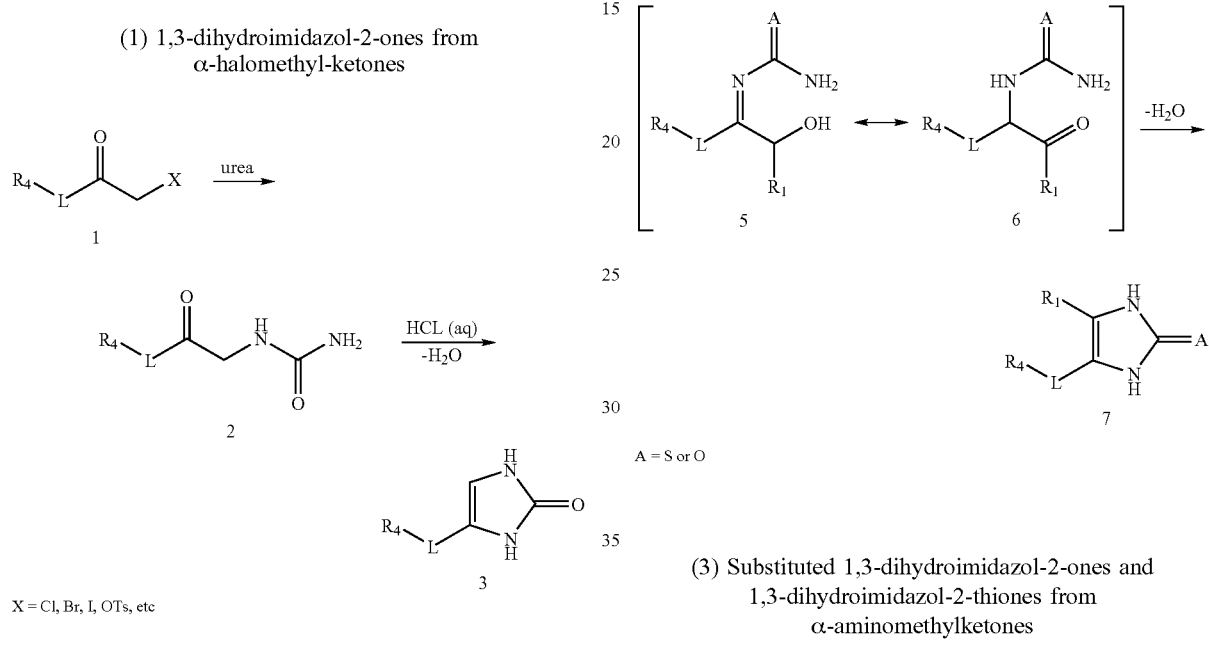

(3) Substituted 1,3-dihydroimidazol-2-ones and 1,3-dihydroimidazol-2-thiones from α-aminomethylketones

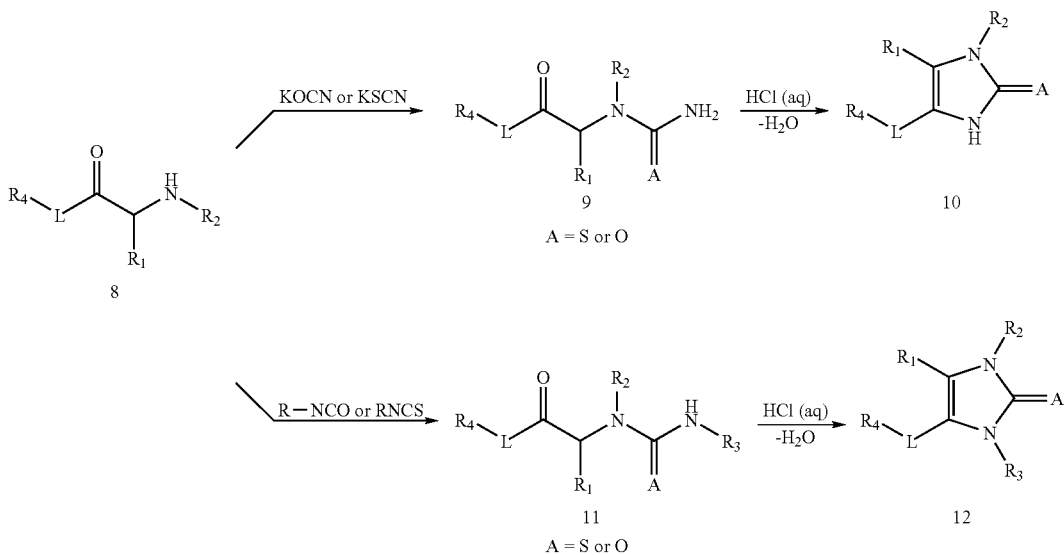

27
(4) 4-Substitution of 1,3-dihydroimidazol-2-one and 1,3-dihydroimidazol-2-thione via the Friedel-Crafts acylation
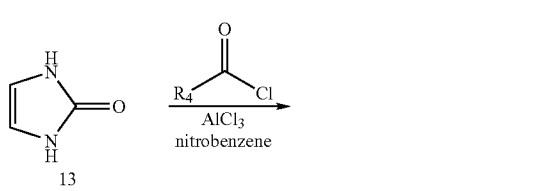
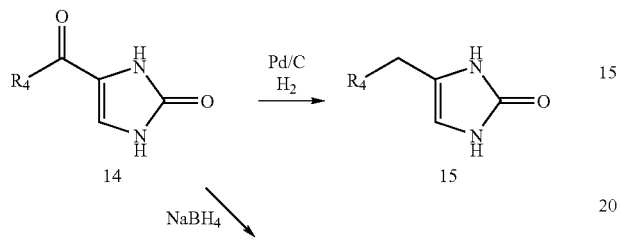
28
-continued
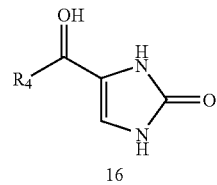
(5) Synthesis of substituted 1,3-dihydroimidazol-2-one and 1,3-dihydroimidazol-2-thione derivatives using protecting groups
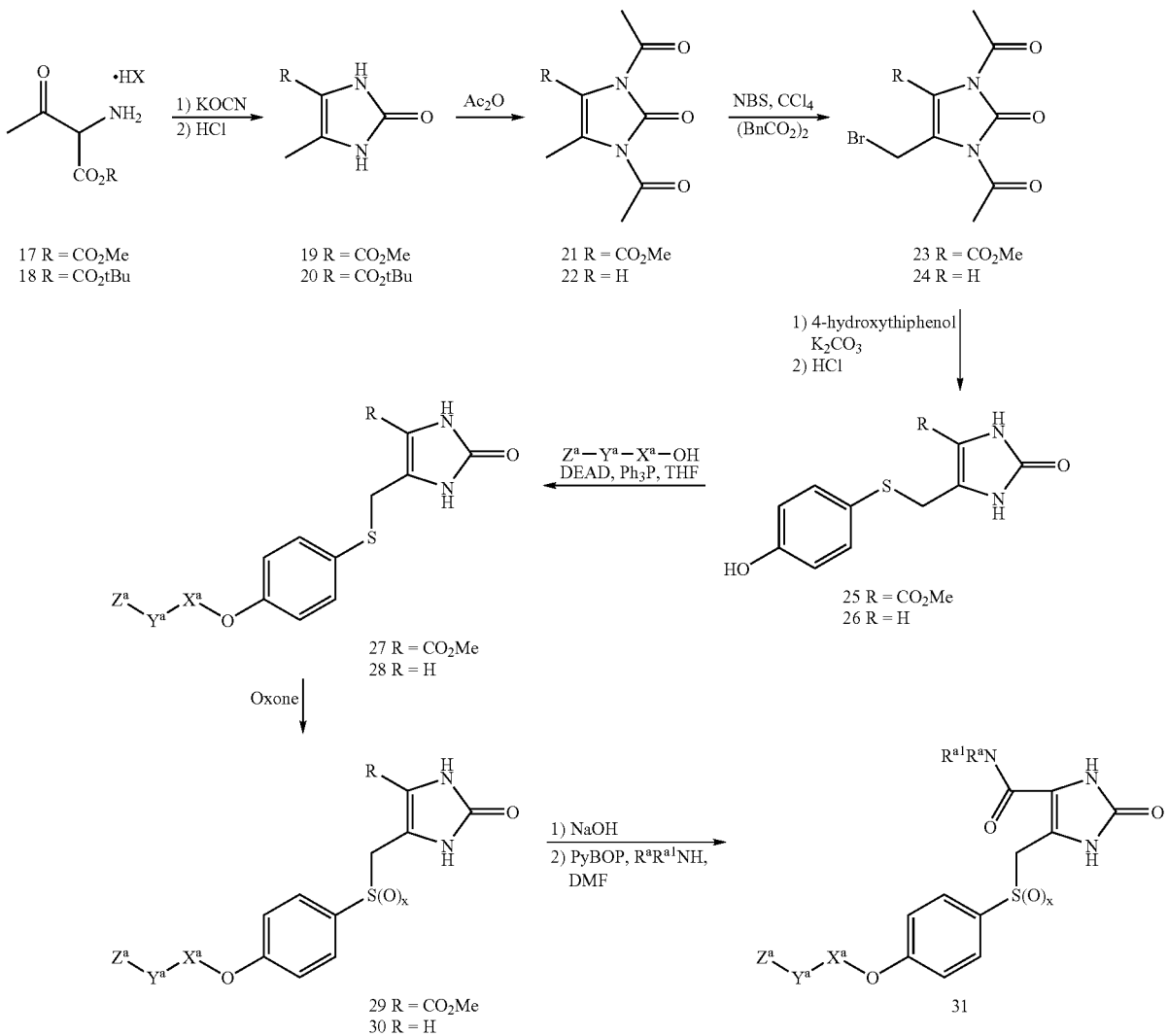

Scheme 1, entry (3) illustrates the synthesis of compounds of Formula I starting from aminomethyl ketones 8 (or salts thereof) which are synthesized using a variety of methods known to one skilled in the art of organic synthesis. Treatment of compound 8 with potassium cyanate or potassium thiocyanate (or equivalents) yields ureidoketone 9 which can be dehydrated under acidic conditions as in entry (1) to give the target heterocycle 10. Alternatively, treatment of compound 8 with isocyanates or isothiocyanates gives a trisubstituted urea intermediate 11 which can cyclize to form the N,N-disubstituted dihydroimidazole(thi)one 12 (see *J. Amer. Chem. Soc.* 1955, 1056; *Arzneim. Forsch./Drug Res.* 1992, 42, 592–594; *J. Chem. Soc.*, 1913, 310–316; and *Chem. Heterocycl. Compnd.* 1986, 22, 1084–1087).

Scheme 1, entry (4) illustrates a convenient and powerful method for introducing substituents in the 4-position of 1,3-dihydroimidazol-2-ones via a Friedel-Crafts-type acylation. The parent heterocycle 13 can be reacted with an acid chloride in the presence of aluminum trichloride and nitrobenzene to give the 4-keto substituted dihydroimidazolones 14 in good yield. The ketone may be reduced completely to the methylene compound 15 using hydrogenation (when R4 is aromatic, see Duschinsky and Dolan *J. Amer. Chem. Soc.* 1946, 68, 2350, 2353) or reduced to the alcohol 16 using hydride reducing agents such as sodium borohydride (*J. Chem. Soc. Perkin Trans I*, 1992, 255–258).

Scheme 1, entry (5) depicts a synthetic route for of 1,3-dihydroimidazol-2-ones where the heterocycle has been doubly protected using acetyl protecting groups. Treatment of 2-amino-3-keto esters 17 and 18 (or their salts) with KOCN gives the corresponding ureido ketones that can be cyclized to the 1,3-dihydroimidazol-2-ones using HCl to give 19 and 20, respectively as in Scheme 1, entry 3. Treatment of compound 19 with acetic anhydride provides an N,N-bisacetyl protected dihydroimidazolone 21. Treatment of the t-butyl ester 20 under the same conditions results in ester deprotection followed by decarboxylation to give the 5-unsubstituted dihydroimidazolinone 22. Reaction of either compounds with N-bromosuccinimide gives efficient methyl bromination, providing compounds 23 and 24. SN2 reaction of these electrophiles with 4-hydroxythiophenol provides the product sulfides which are deprotected using HCl to give compounds 25 and 26. The free hydroxy substituent can be functionalized using a variety of alkylative conditions, shown here is alkylation under Mitsunobu conditions with various primary alcohols to form ethers 27 and 28. The sulfides can be optionally oxidized to sulfoxides or sulfones using Oxone or similar oxidant. Alternatively, ester 27 or 29 can be saponified under basic conditions to give an intermediate carboxylic acid that can be coupled with a variety of amines to give product 31.

All references cited herein are hereby incorporated in their entirety herein by reference.

The following Examples have been prepared, isolated and characterized using the methods disclosed herein. The following Examples demonstrate a partial scope of the invention and are not meant to be limiting of the scope of the invention.

EXAMPLES

Abbreviations used in the Examples are defined as follows: "1×" for once, "2×" for twice, "3×" for thrice, "° C." for degrees Celsius, "eq" for equivalent or equivalents, "g" for gram or grams, "mg" for milligram or milligrams, "µg" for microgram, "mL" for milliliter or milliliters, "µL" for microliter(s), "mmol" for millimolar, "M" for molar, "mM" denotes millimolar, "nM" denotes nanomolar, "µM" denotes micromolar, "nm" for nanometer, "meq" for milliequivalent(s), "min" for minute or minute(s), "atm" for atmosphere, "conc." for concentrated, "MW" for molecular weight, "mp" for melting point, "rt" or "RT" for room temperature, "sat" or "sat'd" for saturated "$^1$H" for proton, "MHz" for megahertz, "MS" for mass spectroscopy, "NMR" for nuclear magnetic resonance spectroscopy, "rt" for room temperature, "tlc" for thin layer chromatography, "v/v" for volume to volume ratio, "ESI" for electrospray ionization mass spectroscopy, "HPLC" for high performance liquid chromatography, "MS" for mass spectrometry, "LC/MS" for liquid chromatography mass spectrometry, "NMR" for nuclear magnetic resonance spectroscopy, and "TLC" for thin layer chromatography. "Sigma" stands for the Sigma-Aldrich Corp. of St. Louis, Mo.

Solution ratio expresses a volume relationship, unless stated otherwise. NMR chemical shifts (δ) are reported in parts per million. Flash chromatography was carried out on silica gel according to Still's method (Still, W. C. et al. *J. Org. Chem.* 1978, 43, 2923).

As used throughout the specification, the following abbreviations for chemical reagents apply:

HOAc or AcOH=acetic acid
Bn=benzyl
Bu=butyl
t-Bu=tertiary butyl
Boc=tert-butyl oxycarbonyl
DMF=dimethylformamide
DMSO=dimethyl sulfoxide
Et=ethyl
EtOH=ethanol
EtOAc=ethyl acetate
Me=methyl
MeOH=methanol
NaOAc=sodium actetate
OAc=acetate
Ph=phenyl
Pr=propyl
i-Pr=isopropyl
i-PrOH=isopropanol
TFA=trifluoroacetic acid
THF=tetrahydrofuran "α", "β", "R", "S", "E", and "Z" are stereochemical designations familiar to one skilled in the art. One stereoisomer of a compound of Formula (I) may display superior activity compared with the others. Thus, each stereoisomer of a compound of Formula (I) is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula (I) may also be directly synthesized using a chiral catalyst or a chiral ligand, e.g., Jacobsen, E. *Acc. Chem. Res.* 2000, 33, 421–431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

4-(2-Methyl-quinolin-4-yl methoxy)-N-[2-(2-oxo-2,3-dihydro-1H-imidazole-4-carbonyl)phenyl]benzamide

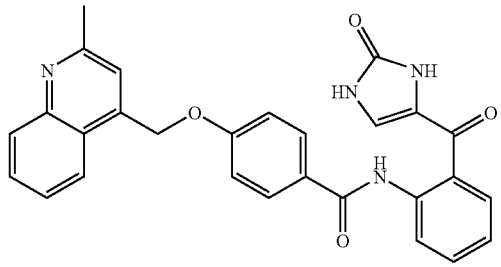

a)

To a solution of dihydroimidazolone 1a (1.0 g, 11.9 mmol) in 24 mL 1M $AlCl_3$ in nitrobenzene was added 2-nitrobenzoyl chloride (2.2 g, 11.9 mmol), and the reaction was heated in a 65° C. oil bath for 6 h. The reaction was poured over ice during which a solid formed. The reaction was filtered through a sintered glass funnel and the solid washed with water and diethyl ether and dried in vacuum dessicator to give 1.26 g (45% yield) of 4-nitrobenzoyl-1,3-dihydroimidazol-2-one 1b.

b)

1b (200 mg, 0.86 mmol) in 20 mL MeOH was hydrogenated over 10% Pd/C (40 mg) at 50 psi $H_2$. The reaction mixture was filtered through a plug of Celite®, washed with MeOH and concentrated on a rotary evaporator to give 168 mg (98% yield) of 4-aminobenzoyl-1,3-dihydroimidazol-2-one 1c. MS found: $(M+H)^+=204$.

c)

To a solution of 4-[(2-methyl-4-quinolinyl)methoxy]benzoic acid (228 mg, 0.78 mmol) in pyridine (2 mL) was added phosphorus oxychloride (181 mg, 1.18 mmol). After 15 min, 1c (100 mg, 0.49 mmol) in 1 mL pyridine was added and the reaction mixture was stirred for 1h then DMAP (10 mol %) was added. The reaction was stirred at rt overnight and then extracted from sat $KH_2PO_4$ with EtOAc×3. The combined organic extracts were dried over $MgSO_4$, filtered, concentrated on a rotary evaporator and purified by reverse-phase HPLC. 15 mg of the product as a TFA salt (6.4% yield) was obtained. MS found: $(M+H)^+=479$.

Example 2

4-(2-Methyl-quinolin-4-yl methyl)-N-[2-(2-oxo-2,3-dihydro-1H-imidazole-4-carbonyl)phenyl]benzamide

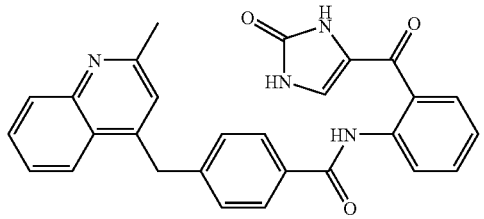

To a solution of 4-[(2-methyl-4-quinolinyl)methyl]benzoic acid (216 mg, 0.78 mmol) in pyridine (2 mL) was added phosphorus oxychloride (181 mg, 1.18 mmol). After 15 min, 1c (100 mg, 0.49 mmol) in 1 mL pyridine was added and the reaction mixture was stirred for 1 h then DMAP (10 mol %) was added. The reaction was stirred at rt overnight and then extracted from sat $KH_2PO_4$ with EtOAc×3. The combined organic extracts were dried over $MgSO_4$, filtered, concentrated on a rotary evaporator and purified by reverse-phase HPLC to give 6 mg of the product as a TFA salt (1.3% yield). MS found: $(M+H)^+=463$.

Example 3

4-(2-Methyl-quinolin-4-yl methoxy)-N-[2-(2-oxo-2,3-dihydro-1H-imidazol-4-yl methyl)phenyl]benzamide

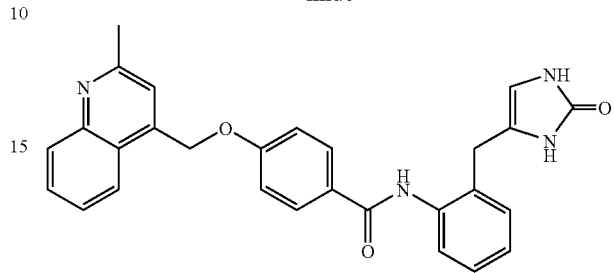

a)

A solution of 1-amino-3-(2-nitrophenyl)-propan-2-one 3a (138 mg, 0.6; Alazard et al. *Tetrahedron* 1994, 50, 6287–6298) in water was reacted potassium cyanate (97 mg, 1.2 mmol) and heated in a 60° C. oil bath for 4 h. The reaction was purified by reverse-phase HPLC to give 82 mg (62% yield) of 4-(2-nitrobenzyl)-1,3-dihydroimidazol-2-one 3b. MS found: $(M+MeCN)^+=261$.

b)

3b (82 mg, 0.37 mmol) in MeOH was hydrogenated over 10% Pd/C (10 mg) at 50 psi $H_2$. The reaction mixture was filtered through a plug of Celite®, washed with MeOH and concentrated on a rotary evaporator to give 69 mg (98% yield) of 4-(2-aminobenzyl)-1,3-dihydroimidazol-2-one 3c. MS found: $(M+H)^+=190$.

c)

To a solution of 4-[(2-methyl-4-quinolinyl)methoxy]benzoic acid (234 mg, 0.8 mmol) in pyridine (2 mL) was added phosphorus oxychloride (181 mg, 1.18 mmol). After 15 min, 3c (115 mg, 0.61 mmol) in 1 mL pyridine was added and the reaction mixture was stirred for 1 h then DMAP (10 mol %) was added. The reaction was stirred at rt o/n and then extracted from sat $KH_2PO_4$ with EtOAc×3. The combined organic extracts were dried over $MgSO_4$, filtered, concentrated on a rotary evaporator and purified by reverse-phase HPLC. 6 mg of the product 4-[(2-methyl-4-quinolinyl)methoxy]-N-[2-(2-oxo-2,3-dihydro-1H-imidazol-4-ylmethyl)-phenyl]-benzamide as a TFA salt (6.4% yield) was obtained. MS found: $(M+H)^+=465$.

Example 4

5-[4-(2-methyl-quinolin-4-ylmethoxy)-benzenesulfonylmethyl]-2-oxo-2,3-dihydro-1H-imidazole-4-carboxylic acid methyl ester

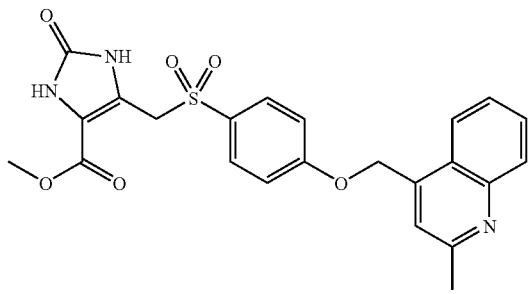

a)

To a solution of 2-amino-3-oxo-butyric acid methyl ester (100 mmol) (Lida, H. et al. *Synthetic Communication,* 1973, 3, 225–230) in 150 mL of ethanol was added KOCN (16.2 g, 200 mmol). The mixture was heated at 80° C. for 2 h. The solution was acidified with 2 N HCl and concentrated to half of the volume in vacuo. The product precipitated out upon cooling. Filtration, followed by washing with water, provided 5-methyl-2-oxo-2,3-dihydro-1H-imidazole-4-carboxylic acid methyl ester 4a (15 g, >95%). MS (ESI$^+$) (M+1)=157.

b)

4a (6 g, 38.4 mmol) was dissolved in 40 mL of acetic anhydride and the solution was refluxed overnight. Removal of excess acetic anhydride and acetic acid provided 2-acetoxy-1-acetyl-5-methyl-1H-imidazole-4-carboxylic acid methyl ester 4b (9.0 g, 97%). MS (ESI$^+$) (M+1)=241.2.

c)

To a solution of 4b (9.0 g, 38 mmol) in 300 mL of CCl$_4$ was added N-bromosuccinimide (7.1 g, 40 mmol) and benzoyl peroxide (80 mg). The solution was refluxed for 4 h and then cooled down to rt. Succinimide was then removed through filtration and the filtrate was concentrated to provide 2-acetoxy-1-acetyl-5-bromomethyl-1H-imidazole-4-carboxylic acid methyl ester 4c (12 g, 95%). MS (ESI$^+$) (M+1)=318.9, 320.9.

d)

To a solution of 4c (640 mg, 2 mmol) in 20 mL of MeOH was added 4-mercaptophenol (380 mg, 3.0 mmol) and K$_2$CO$_3$ (550 mg, 4.0 mmol). The solution was stirred at rt for 6 h. 20 mL of water was then added and 2 mL of 1N HCl was carefully added. This aqueous solution was extracted with Et$_2$O. The aqueous solution was then concentrated and the residue was first dissolved in 5 mL of MeOH and the diluted with 50 mL of CH$_2$Cl$_2$. Filtration and concentration provided 5-(4-hydroxy-phenylsulfanyl methyl)-2-oxo-2,3-dihydro-1H-imidazole-4-carboxylic acid methyl ester 4d (440 mg, 80%). MS (ESI$^+$) (M+AcN+1)=322.

e)

To a solution of DEAD (81 mg, 0.46 mmol) in 3 mL of THF at 0° C. was added PPh$_3$ (120 mg, 0.46 mmol). After dissolution of PPh$_3$, 4d (100 mg, 0.31 mmol) was added and the solution was stirred for 15 min. (2-methyl-4-quinolinyl) methanol was then added as a solid. After stirring for 2 h, 3 mL of DMF was added to aid dissolution. The mixture was stirred at room temperature overnight before it was quenched with water. The solution was extracted with CH$_2$Cl$_2$ and the organic layer was dried over MgSO$_4$. After filtration and concentration, the residue was purified by flash column chromatography to provide 5-[4-(2-methyl-quinolin-4-ylmethoxy)-phenylsulfanylmethyl]-2-oxo-2,3-dihydro-1H-imidazole-4-carboxylic acid methyl ester 4e (11 mg, 8%). MS (ESI$^+$) (M+1)=436.

f)

To a solution of 4e (11 mg, 0.025 mmol) in 5 mL of a mixture of THF:MeOH:H$_2$O (2:1:2) was added a solution of Oxone® (31 mg, 0.05 mmol) in H$_2$O, buffered with NaHCO$_3$ (0.05 mmol). The solution was stirred at 0° C. for 1 h and filtered. The filtrate was concentrated and purified by flash column chromatography to provide 5-[4-(2-methyl-quinolin-4-ylmethoxy)-benzenesulfonylmethyl]-2-oxo-2,3-dihydro-1H-imidazole-4-carboxylic acid methyl ester 4f (10 mg, 85%). MS (ESI$^+$) (M+1)=468.

Example 5

4-[4-(2-methyl-quinolin-4-ylmethoxy)-phenylsulfanylmethyl]-1,3-dihydro-imidazol-2-one

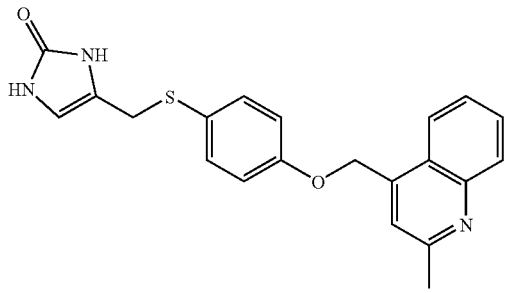

a)

Following a procedure similar to step 4a, 2-amino-3-oxo-butyric acid tert-butyl ester (17.3 g, 100 mmol) was converted to 5-methyl-2-oxo-2,3-dihydro-1H-imidazole-4-carboxylic acid tert-butyl ester (19.1 g, 96%). MS (ESI$^+$) (2M+1)=397.3.

b)

Following a procedure similar to step 4b, 5-methyl-2-oxo-2,3-dihydro-1H-imidazole-4-carboxylic acid tert-butyl ester (9.5 g, 48 mmol) was converted to acetic acid 1-acetyl-4-methyl-1H-imidazol-2-yl ester (8.0 g, 92%). MS (ESI$^+$) (M+1)=182.9.

c)

Following a procedure similar to step 4c, acetic acid 1-acetyl-4-methyl-1H-imidazol-2-yl ester (8.0 g, 44 mmol) was converted to acetic acid 1-acetyl-4-bromomethyl-1H-imidazol-2-yl ester (10 g, 87%). MS (ESI$^+$) (M+1)=262.1.

d)

Following a procedure similar to step 4d, acetic acid 1-acetyl-4-bromomethyl-1H-imidazol-2-yl ester (520 mg, 2 mmol) was converted to 4-(4-hydroxy-phenylsulfanylmethyl)-1,3-dihydro-imidazol-2-one (330 mg, 74%). MS (ESI$^+$) (M+1)=223.

e)

Following a procedure similar to step 4e, 4-(4-hydroxy-phenylsulfanylmethyl)-1,3-dihydro-imidazol-2-one (65 mg, 0.3 mmol) was converted to 4-[4-(2-methyl-quinolin-4-ylmethoxy)-phenylsulfanylmethyl]-1,3-dihydro-imidazol-2-one (45 mg, 40%). MS (ESI$^+$) (M+1)=378.

Example 6

4-[4-(2-methyl-quinolin-4-ylmethoxy)-benzenesulfinylmethyl]-1,3-dihydro-imidazol-2-one

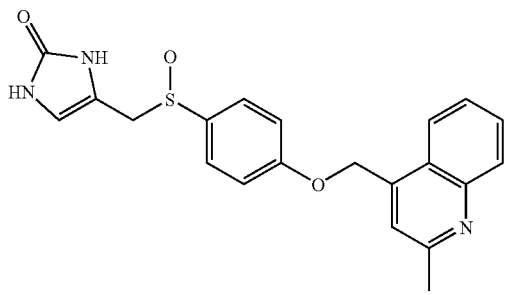

Following a procedure similar to step 4f, 4-[4-(2-methyl-quinolin-4-ylmethoxy)-phenylsulfanylmethyl]-1,3-dihydro-imidazol-2-one (35 mg, 0.09 mmol) was converted to 4-[4-

(2-Methyl-quinolin-4-ylmethoxy)-benzenesulfinylmethyl]-1,3-dihydro-imidazol-2-one (5 mg, 14%). MS (ESI$^+$) (M+1)=394.

Example 7

4-[4-(2-Methyl-quinolin-4-ylmethoxy)-benzenesulfonylmethyl]-1,3-dihydro-imidazol-2-one

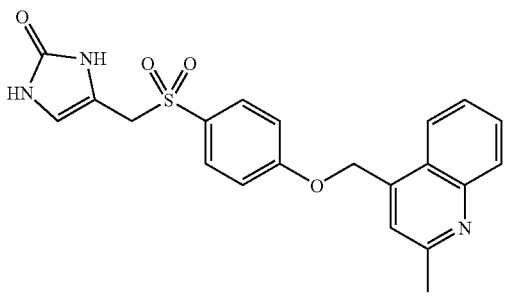

Following a procedure similar to step 4f, 4-[4-(2-methyl-quinolin-4-ylmethoxy)-phenylsulfanylmethyl]-1,3-dihydro-imidazol-2-one (35 mg, 0.09 mmol) was converted to 4-[4-(2-Methyl-quinolin-4-ylmethoxy)-benzenesulfonylmethyl]-1,3-dihydro-imidazol-2-one (15 mg, 41%). MS (ESI$^+$) (M+1)=410.

Utility

The compounds of the present invention are expected to possess matrix metalloproteinase and/or aggrecanase and/or TNF-α inhibitory activity. The MMP inhibitory activity of the compounds of the present invention is demonstrated using assays of MMP activity, for example, using the assay described below for assaying inhibitors of MMP activity. The compounds of the present invention are expected to be bioavailable in vivo as demonstrated, for example, using the ex vivo assay described below. The compounds of the present invention are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis (Stetler-Stevenson, *Cancer and Metastasis Reviews*, 1990, 9, 289–303). The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone that occurs in osteoporosis patients.

Compounds that inhibit the production or action of TACE and/or Aggrecanase and/or MMP's are potentially useful for the treatment or prophylaxis of various inflammatory, infectious, immunological or malignant diseases or conditions. Thus, the present invention relates to a method of treating various inflammatory, infectious, immunological or malignant diseases. These include acute infection, acute phase response, age related macular degeneration, alcoholic liver disease, allergy, allergic asthma, anorexia, aneurism, aortic aneurism, asthma, atherosclerosis, atopic dermatitis, autoimmune disease, autoimmune hepatitis, Bechet's disease, cachexia (including cachexia resulting from cancer or HIV), calcium pyrophosphate dihydrate deposition disease, cardiovascular effects, chronic fatigue syndrome, chronic obstruction pulmonary disease, coagulation, congestive heart failure, corneal ulceration, Crohn's disease, enteropathic arthropathy (including inflammatory bowel disease), Felty's syndrome, fever, fibromyalgia syndrome, fibrotic disease, gingivitis, glucocorticoid withdrawal syndrome, gout, graft versus host disease, hemorrhage, HIV infection, hyperoxic alveolar injury, infectious arthritis, inflammation, intermittent hydrarthrosis, Lyme disease, meningitis, multiple sclerosis, myasthenia gravis, mycobacterial infection, neovascular glaucoma, osteoarthritis, pelvic inflammatory disease, periodontitis, polymyositis/dermatomyositis, post-ischaemic reperfusion injury, post-radiation asthenia, psoriasis, psoriatic arthritis, pulmonary emphysema, pydoderma gangrenosum, relapsing polychondritis, Reiter's syndrome, rheumatic fever, rheumatoid arthritis (including juvenile rheumatoid arthritis and adult rheumatoid arthritis), sarcoidosis, scleroderma, sepsis syndrome, Still's disease, shock, Sjogren's syndrome, skin inflammatory diseases, solid tumor growth and tumor invasion by secondary metastases, spondylitis, stroke, systemic lupus erythematosus, ulcerative colitis, uveitis, vasculitis, and Wegener's granulomatosis.

Some compounds of the present invention have been shown to inhibit TNF production in lipopolysacharride stimulated mice, for example, using the assay for TNF induction in mice and in human whole blood as described below.

Some compounds of the present invention have been shown to inhibit aggrecanase, a key enzyme in cartilage breakdown, as determined by the aggrecanase assay described below.

The compounds of the present invention can be administered alone or in combination with one or more additional anti-inflammatory agents. These agents include, but are not limited to, selective COX-2 inhibitors, interleukin-1 antagonists, dihydroorotate synthase inhibitors, p38 MAP kinase inhibitors, TNF-α inhibitors, and TNF-α sequestration agents.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term selective COX-2 inhibitors, as used herein, denote agents that selectively inhibit COX-2 function. Such agents include, but are not limited to, celecoxib (Celebrex®), rofecoxib (Vioxx®), meloxicam (Movicox®), etoricoxib, and valdecoxib.

TNF-α sequestration agents that may be used in combination with the compounds of this invention, are TNF-α binding proteins or anti-TNF-α antibodies. These agents include, but are not limited to, etanercept (Enbrel®), infliximab (Remicade®), adalimumab (D2E7), CDP-571 (Humicade®), and CDP-870.

Other anti-inflammatory agents that may be used in combination with the compounds of this invention, include, but are not limited to, methotrexate, interleukin-1 antagonists (e.g., anakinra (Kineret®)), dihydroorotate synthase inhibitors (e.g., leflunomide (Arava®)), and p38 MAP kinase inhibitors.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention can be used for making a coating on an implantable medical device, more particularly, on a stent, is particularly advantageous in reducing the restinosis or thrombosis associated with introduction of the stent into the mammalian body.

Besides the TACE inhibitor, one or more additional therapeutic agents may be incorporated into the stent coating to provide an additive or synergistic therapeutic advantage. For example, such additional therapeutic agents include, but not limited to: antiproliferative/antimitotic agents including natural 12 products such as vinca alkaloids (i.e., vinblastine, vincristine, and vinorelbine), paclitaxel, epidipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L asparagine and deprives cells which don't have the capacity to synthesize their own asparagine); antiproliferative/antimitotic alkylating agents such as nitrogen mustards(mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and is analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2 chlorodeoxyadenosine(cladribine)); platinum coordination complexes (cisplatin, carboplatin), procarbazine, hydroxyurea, mitotane, aminoglutethimide; hormones (i.e. estrogen); Anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisclone, 6(x methylprednisolone, triamcinolone, betamethasone, and dexamethasone), non-steroidal agents (salicylic acid 13 derivatives i.e., aspirin; para-aminophenol derivatives i.e. acetominophen; Indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); Angiogenic agents: vascular endothelial growth factor (VEGF), fibroblast growth factor (FGF); nitric oxide donors; cell cycle inhibitors; mTOR inhibitors; growth factor signal transduction knase inhibitors; anti sense oligonucleotide; prodrug molecules; and combinations thereof.

As used herein "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar and "nm" denotes nanometer. "Sigma stands for the Sigma-Aldrich Corp. of St. Louis, Mo.

A compound is considered to be active if it has an $IC_{50}$ or $K_i$ value of less than about 10 µM for the inhibition of a desired MP. Preferred compounds of the present invention have $K_i$'s or $IC_{50}$'s of $\leq 1$ µM. More preferred compounds of the present invention have $K_i$'s or $IC_{50}$'s of $\leq 0.1$ µM. Even more preferred compounds of the present invention have $K_i$'s or $IC_{50}$'s of $\leq 0.01$ µM. Still more preferred compounds of the present invention have $K_i$'s or $IC_{50}$'s of $\leq 0.001$ µM.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanases time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNF-α) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media (Tortorella, M. D. et al. *Trans. Ortho. Res. Soc.* 1995, 20, 341). Therefore, in order to accumulate BNC aggrecanase in culture media, cartilage is first depleted of endogenous aggrecan by stimulation with 500 mg/mL human recombinant IL-β for 6 days with media changes every 2 days. Cartilage is then stimulated for an additional 8 days without media change to allow accumulation of soluble, active aggrecanase in the culture media. In order to decrease the amount of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, C. E. et al., *Biochem. J.* 1995, 306, 799–804). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 µM for aggrecanase.

To evaluate inhibition of aggrecanase, compounds are prepared as 10 mM stocks in DMSO, water or other solvents and diluted to appropriate concentrations in water. Drug (50 µL) is added to 50 µL of aggrecanase-containing media and 50 µL of 2 mg/mL aggrecan substrate and brought to a final volume of 200 µL in 0.2 M Tris, pH 7.6, containing 0.4 M NaCl and 40 mM CaCl$_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 μl of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

TNF PBMC Assays

Human peripheral blood mononuclear cells (PBMC) were obtained from normal donor blood by leukophoresis and isolated by Ficoll-Paque density separation. PBMCs were suspended in 0.5 mL RPMI 1640 with no serum at 2×10$^6$ cells/mL in 96 well polystyrene plates. Cells were preincubated 10 minutes with compound, then stimulated with 1 μg/mL LPS (Lipopolysaccharide, Salmonella typhimurium) to induce TNF production. After an incubation of 5 hours at 37° C. in 95% air, 5% CO$_2$ environment, culture supernatants were removed and tested by standard sandwich ELISA for TNF production.

TNF Human Whole Blood Assay

Blood is drawn from normal donors into tubes containing 143 USP units of heparin/10 mL. 225 μl of blood is plated directly into sterile polypropylene tubes. Compounds are diluted in DMSO/serum free media and added to the blood samples so the final concentration of compounds are 50, 10, 5, 1, 0.5, 0.1, and 0.01 μM. The final concentration of DMSO does not exceed 0.5%. Compounds are preincubated for 15 minutes before the addition of 100 mg/mL LPS. Plates are incubated for 5 hours in an atmosphere of 5% CO$_2$ in air. At the end of 5 hours, 750 μl of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC$_{50}$ value.

TNF Induction in Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

MMP Assays

The enzymatic activities of recombinant MMP-1, 2, 3, 7, 8, 9, 10, 12, 13, 14, 15, and 16 were measured at 25° C. with a fluorometric assay (Copeland, R. A. et al. *Bioorganic Med Chem. Lett.* 1995, 5, 1947–1952). Final enzyme concentrations in the assay were between 0.05 and 10 nM depending on the enzyme and the potency of the inhibitor tested. The permissive peptide substrate, MCA-Pro-Leu-Gly-Leu-DPA-Ala-Arg-NH$_2$, was present at a final concentration of 10 μM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. Enzymes: *A practical Introduction to Structure, Mechanism and Data Analysis*, Wiley-VHC, New York, 1996, pp 187–223). All of the compounds studied here were assumed to act as competitive inhibitors of the enzyme, binding to the active site Zn atom as previously demonstrated by crystallographic studies of MMP-3 complexed with related hydroxamic acids (Rockwell, A. et al. *J. Am. Chem. Soc.* 1996, 118, 10337–10338). Based on the assumption of competitive inhibition, the IC$_{50}$ values were converted to K$_i$ values as previously described.

Compounds tested in the above assay are considered to be active if they exhibit a K$_i$ of ≦10 μM. Preferred compounds of the present invention have K$_i$'s of ≦1 μM. More preferred compounds of the present invention have K$_i$'s of ≦0.1 μM. Even more preferred compounds of the present invention have K$_i$'s of ≦0.01 μM. Still more preferred compounds of the present invention have K$_i$'s of ≦0.001 μM.

Using the methodology described above, a number of compounds of the present invention were found to exhibit K$_i$'s of ≦10 μM, thereby confirming the utility of the compounds of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences,* Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolytic agent when administered alone may be reduced by about 70–80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound of Formula (I):

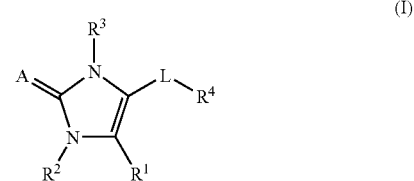

(I)

or a stereoisomer or pharmaceutically acceptable salt or solvate thereof, wherein:

A is O or S;

L is a bond, CO, CH(OH), or $CR^5R^6$;

$R^1$ is Q, F, Cl, Br, I, CN, $NO_2$, $-CF_2CF_3$, $-NR^7R^8$, $C_{1-4}$ haloalkyl, $-C_{1-6}$ alkylene-Q, $-C_{2-6}$ alkenylene-Q, $-C_{2-6}$ alkynylene-Q, $-(CR^aR^{a1})_rO(CR^aR^{a1})_s$-Q, $-(CR^aR^{a1})_rNR^a(CR^aR^{a1})_s-Q$, $-(CR^aR^{a1})_rC(O)(CR^aR^{a1})_s-Q$, $-(CR^aR^{a1})_rC(O)O(CR^aR^{a1})_s-Q$, $-(CR^aR^{a1})_rOC(O)(CR^aR^{a1})_s-Q$, $-(CR^aR^{a1})_rC(O)NR^aR^{a1}$, $-(CR^aR^{a1})_rC(O)NR^a(CR^aR^{a1})_s-Q$, $-(CR^aR^{a1})_rNR^aC(O)(CR^aR^{a1})_s-Q$, $-(CR^aR^{a1})_rOC(O)O(CR^aR^{a1})_s-Q$, $-(CR^aR^{a1})_rOC(O)NR^a(CR^aR^{a1})_s-Q$, $-(CR^aR^{a1})_rNR^aC(O)O(CR^aR^{a1})_s-Q$, $-(CR^aR^{a1})_rNR^aC(O)NR^a(CR^aR^{a1})_s-Q$, $-(CR^aR^{a1})_rS(CR^aR^{a1})_s-Q$, $-(CR^aR^{a1})_rS(O)(CR^aR^{a1})_s-Q$, $-(CR^aR^{a1})_rS(O)_2(CR^aR^{a1})_s-Q$, $-(CR^aR^{a1})_rSO_2NR^a(CR^aR^{a1})_s-Q$, $-(CR^aR^{a1})_rNR^aSO_2-(CR^aR^{a1})_s-Q$, or $-(CR^aR^{a1})_rNR^aSO_2NR^a(CR^aR^{a1})_s-Q$;

$R^2$ is H, $C_{1-4}$ alkyl, $C_{2-4}$ alkenyl, or $C_{2-4}$ alkynyl;

$R^3$ is H, $C_{1-4}$ alkyl, $C_{2-4}$ alkenyl, or $C_{2-4}$ alkynyl;

$R^4$ is $-Z^0-W-U-X-Y-Z-U^aX^a-Y^a-Z^a$;

$R^5$ is Q, $-C_{1-6}$ alkylene-Q, $-C_{2-6}$ alkenylene-Q, $-C_{2-6}$ alkynylene-Q, $-(CR^aR^{a1})_rO(CR^aR^{a1})_s-Q$, $-(CR^aR^{a1})_rNR^a(CR^aR^{a1})_s-Q$, $-(CR^aR^{a1})_rC(O)(CR^aR^{a1})_s-Q$, $-(CR^aR^{a1})_rC(O)O(CR^aR^{a1})_s-Q$, —(CR$^a$R$^{a1}$)$_r$OC(O)(CR$^a$R$^{a1}$)$_s$—Q, —(CR$^a$R$^{a1}$)$_r$C(O) NR$^a$R$^{a1}$, —(CR$^a$R$^{a1}$)$_r$C(O)NR$^a$(CR$^a$R$^{a1}$)$_s$—Q, —(CR$^a$R$^{a1}$)$_r$NR$^a$C(O)(CR$^a$R$^{a1}$)$_s$—Q, —(CR$^a$R$^{a1}$)$_r$OC(O)O(CR$^a$R$^{a1}$)$_s$—Q, —(CR$^a$R$^{a1}$)$_r$OC(O)NR$^a$(CR$^a$R$^{a1}$)$_s$—Q, —(CR$^a$R$^{a1}$)$_r$NR$^a$C(O)O(CR$^a$R$^{a1}$)$_s$—Q, —(CR$^a$R$^{a1}$)$_r$NR$^a$C(O)NR$^a$(CR$^a$R$^{a1}$)$_s$—Q, —(CR$^a$R$^{a1}$)$_r$S(O)$_p$(CR$^a$R$^{a1}$)$_s$—Q, —(CR$^a$R$^{a1}$)$_r$SO$_2$NR$^a$ (CR$^a$R$^{a1}$)$_s$—Q, —(CR$^a$R$^{a1}$)$_r$NR$^a$SO$_2$—(CR$^a$R$^{a1}$)$_s$—Q, or —(CR$^a$R$^{a1}$)$_r$NR$^a$SO$_2$NR$^a$(CR$^a$R$^{a1}$)$_s$—Q;

R$^6$ is Q, —C$_{1-6}$ alkylene-Q, —C$_{2-6}$ alkenylene-Q, —C$_{2-6}$ alkynylene-Q, —(CR$^a$R$^{a1}$)$_r$O(CR$^a$R$^{a1}$)$_s$—Q, —(CR$^a$R$^{a1}$)$_r$NR$^a$(CR$^a$R$^{a1}$)$_s$—Q, —(CR$^a$R$^{a1}$)$_r$C(O) (CR$^a$R$^{a1}$)$_s$—Q, —(CR$^a$R$^{a1}$)$_r$C(O)O(CR$^a$R$^{a1}$)$_s$—Q, —(CR$^a$R$^{a1}$)$_r$C(O)NR$^a$R$^{a1}$, —(CR$^a$R$^{a1}$)$_r$C(O)NR$^a$ (CR$^a$R$^{a1}$)$_s$—Q, —(CR$^a$R$^{a1}$)$_r$NR$^a$C(O)(CR$^a$R$^{a1}$)$_s$—Q, —(CR$^a$R$^{a1}$)$_r$S(O)$_p$(CR$^a$R$^{a1}$)$_s$—Q, —(CR$^a$R$^{a1}$)$_r$ SO$_2$NR$^a$(CR$^a$R$^{a1}$)$_s$—Q, or —(CR$^a$R$^{a1}$)$_r$NR$^a$SO$_2$—(CR$^a$R$^{a1}$)$_s$—Q;

R$^7$ is H, C$_{1-6}$ alkyl, C$_{2-6}$ alkenyl, C$_{2-6}$ alkynyl, —C$_{1-6}$ alkylene-Q$^1$, —C$_{2-6}$ alkenylene-Q$^1$, —C$_{2-6}$ alkynylene-Q$^1$, —(CR$^a$R$^{a1}$)$_r$C(O)(CR$^a$R$^{a1}$)$_s$-Q$^1$, —(CR$^a$R$^{a1}$)$_r$C(O) O(CR$^a$R$^{a1}$)$_s$—Q$^1$, —(CR$^a$R$^{a1}$)$_r$C(O)O(CR$^a$R$^{a1}$)$_t$OC (O)$_s$—Q$^1$, —(CR$^a$R$^{a1}$)$_r$C(O)NH(CR$^a$R$^{a1}$)$_s$—Q$^1$, or —(CR$^a$R$^{a1}$)$_r$S(O)$_2$)(CR$^a$R$^{a1}$)$_s$—Q$^1$;

R$^8$ is H, C$_{1-6}$ alkyl, or —(CH$_2$)$_n$-phenyl;

alternatively, R$^7$ and R$^8$ combine to form a 5–10 membered heterocyclic ring consisting of carbon atoms and 0–2 additional heteroatoms selected from the group consisting of N, O, and S(O)$_p$;

each R$^9$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O) OR$^{a1}$, —(CR$^a$R$^{a1}$)$_r$C(S)OR$^{a1}$, —(CR$^a$R$^{a1}$)$_r$C(O) NR$^a$R$^{a1}$, —(CR$^a$R$^{a1}$)$_r$C(S)NR$^a$R$^{a1}$, —(CR$^a$R$^{a1}$)$_r$NR$^a$C (O)R$^{a1}$, —(CR$^a$R$^{a1}$)$_r$OC(O)NR$^a$R$^{a1}$, —(CR$^a$R$^{a1}$)$_t$ NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)SO$_2$NR$^a$R$^{a1}$, —(CR$^a$R$^{a1}$)$_r$NR$^a$SO$_2$R$^{a3}$, —(CR$^a$R$^{a1}$)$_t$ NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$; or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

each R$^{10}$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O) OR$^{a1}$, —(CR$^a$R$^{a1}$)$_r$C(S)OR$^{a1}$, —(CR$^a$R$^{a1}$)$_r$C(O) NR$^a$R$^{a1}$, —(CR$^a$R$^{a1}$)$_r$C(S)NR$^a$R$^{a1}$, —(CR$^a$R$^{a1}$)$_r$NR$^a$C (O)R$^{a1}$, —(CR$^a$R$^{a1}$)$_r$OC(O)NR$^a$R$^{a1}$, —(CR$^a$R$^{a1}$)$_r$ NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$ NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$; or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

each Q is, independently at each occurrence, H, CF$_3$, —CH$_2$F, —CHF$_2$, C$_{1-6}$ alkyl, a C$_{3-13}$ carbocycle substituted with 0–5 R$^d$, or a 5–12 membered heterocycle consisting of carbon atoms and 1–4 heteroatoms selected from the group consisting of NR$^9$, O, and S(O)$_p$, and substituted with 0–5 R$^d$;

each Q$^1$ is, independently at each occurrence, C$_{1-6}$ alkyl, a C$_{3-13}$ carbocycle substituted with 0–5 R$^d$, or a 5–12 membered heterocycle consisting of carbon atoms and 1–4 heteroatoms selected from the group consisting of NR$^9$, O, and S(O)$_p$, and substituted with 0–5 R$^d$;

Z$^0$ is aryl or a 5–6 membered heteroaryl consisting of carbon atoms and 0–3 ring heteroatoms selected from O, N, NR$^9$, and S, and substituted with 0–3 R$^{10}$ ; and the aryl or heteroaryl is optionally fused to a 5–6 membered carbocycle or heterocycle consisting of carbon atoms and 0–2 ring heteroatoms selected from O, N, NR$^9$, and S(O)$_p$, and 0–2 double bonds, and substituted with 0–3 R$^{10}$;

W is (CR$^a$R$^{a1}$)$_m$, C$_{2-3}$ alkenylene, or C$_{2-3}$ alkynylene;

U is O, C(O), CR$^a$(OH), C(O)O, OC(O), C(O)NR$^{a1}$, OC(O)O, OC(O)NR$^{a1}$, NR$^{a1}$C(O)O, S(O)$_p$, S(O)$_p$ NR$^{a1}$, NR$^{a1}$S(O)$_p$, or NR$^{a1}$SO$_2$NR$^{a1}$;

X is a bond, C$_{1-3}$ alkylene, C$_{2-3}$ alkenylene, or C$_{2-3}$ alkynylene;

Y is a bond, O, NR$^{a1}$, S(O)$_p$, or C(O);

alternatively, Z$^0$ is absent, and W—U—X—Y forms S(O)$_p$;

Z is a C$_{3-13}$ carbocycle substituted with 0–5 R$^b$, or a 5–14 membered heterocycle consisting of carbon atoms and 1–4 heteroatoms selected from the group consisting of N, O, and S(O)$_p$ and substituted with 0–5 R$^b$;

U$^a$ is a bond, O, NR$^{a1}$, C(O), CR$^a$(OH), C(O)O, OC(O), C(O)NR$^{a1}$, NR$^{a1}$C(O), OC(O)O, OC(O)NR$^{a1}$, NR$^{a1}$C (O)O, NR$^{a1}$C(O)NR$^{a1}$, S(O)$_p$, S(O)$_p$NR$^{a1}$, NR$^{a1}$S(O)$_p$, or NR$^{a1}$SO$_2$NR$^{a1}$;

X$^a$ is a bond, C$_{0-10}$ alkylene, C$_{2-10}$ alkenylene, or C$_{2-10}$ alkynylene;

Y$^a$ is a bond, O, NR$^{a1}$, S(O)$_p$, or C(O);

Z$^a$ is a C$_{3-13}$ carbocycle substituted with 0–5 R$^c$, or a 5–14 membered heterocycle consisting of carbon atoms and 1–4 heteroatoms selected from the group consisting of N, O, and S(O)$_p$ and substituted with 0–5 R$^c$;

provided that U, Y, Z, U$^a$, Y$^a$, and Z$^a$ do not combine to form a N—N, N—O, O—N, O—O, S(O)$_p$—O, O—S (O)$_p$ or S(O)$_p$—S(O)$_p$ group;

each R$^a$ is, independently at each occurrence, H, C$_{1-6}$ alkyl, phenyl, or benzyl;

each R$^{a1}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic or heterocyclic ring consisting of carbon atoms and 0–2 ring heteroatoms selected from N, NR$^{a2}$, O, and S(O)$_p$, and substituted with 0–3 R$^{c1}$;

alternatively, R$^a$ and R$^{a1}$ when attached to a nitrogen, together with the nitrogen to which they are attached, combine to form a 5 or 6 membered heterocycle consisting of carbon atoms and from 0–1 additional heteroatoms selected from N, NR$^{a2}$, O, and S(O)$_p$;

each R$^{a2}$ is, independently at each occurrence, C$_{1-4}$ alkyl, phenyl, or benzyl;

each R$^{a3}$ is, independently at each occurrence, H, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, or —(CH$_2$)$_r$-3–8 membered carbocyclic or heterocyclic ring consisting of carbon atoms and 0–2 ring heteroatoms selected from N, NR$^{a2}$, O, and S(O)$^p$, and substituted with 0–3 R$^{c1}$;

each R$^b$ is, independently at each occurrence, C$_{1-6}$ alkyl substituted with 0–1 R$^{c1}$, OR$^a$, SR$^a$, Cl, F, Br, I, =O, —CN, NO$_2$, NR$^a$R$^{a1}$, C(O)R$^a$, —C(O)OR$^a$, —C(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, S(O)$_p$R$^{a3}$, CF$_3$, CF$_2$CF$_3$, CHF$_2$, CH$_2$F, or phenyl;

each R$^c$ is, independently at each occurrence, H, Cl, F, Br, I, =O, CN, NO$_2$, CF$_3$, CF$_2$CF$_3$, CH$_2$F, CHF$_2$, —(CR$^a$R$^{a1}$)$_r$OR$^a$, —(CR$^a$R$^{a1}$)$_r$NR$^a$R$^{a1}$, —(CR$^a$R$^{a1}$)$_r$C(=NCN)NR$^a$R$^{a1}$, —(CR$^a$R$^{a1}$)$_r$C(=NR$^a$)NR$^a$R$^{a1}$, —(CR$^a$R$^{a1}$)$_r$C(=NOR$^a$)NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$_{a1}$, —(CR$^a$R$^{a1}$)$_r$C(S)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$C(S)NR$^a$R$^{a1}$, —(CR$^a$R$^{a1}$)$_r$OC(O)NR$^a$R$^{a1}$, —(CR$^a$R$^{a1}$)$_r$NR$^a$C(O)OR$^{a1}$, —(CR$^a$R$^{a1}$)$_r$NR$^a$C(O)NR$^a$R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, —(CR$^a$R$^{a1}$)$_r$NR$^a$SO$_2$NR$^a$R$^{a1}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$, or —(CR$^a$R$^{a1}$)$_r$-5–14 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds;

each R$^{c1}$ is, independently at each occurrence, H, C$_{1-4}$ alkyl, OR$^a$, Cl, F, Br, I, =O, CF$_3$, CN, NO$_2$, C(O)R$^a$, —C(O)OR$^a$, —C(O)NR$^a$R$^{a1}$, or —S(O)$_p$R$^a$;

each R$^d$ is, independently at each occurrence, C$_{1-6}$ alkyl, OR$^a$, Cl, F, Br, I, =O, CN, NO$_2$, NR$^a$R$^{a1}$, C(O)R$^a$, —C(O)OR$^a$, —(O)NR$^a$R$^{a1}$, —C(S)NR$^a$R$^{a1}$, —NR$^a$C(O)NR$^a$R$^{a1}$, —OC(O)NR$^a$R$^{a1}$, —NR$^a$C(O)OR$^a$, —S(O)$_2$NR$^a$R$^{a1}$, —NR$^a$S(O)$_2$R$^{a3}$, —NR$^a$S(O)$_2$NR$^a$R$^{a1}$, —OS(O)$_2$NR$^a$R$^{a1}$, —S(O)$_p$R$^{a3}$, CF$_3$, CF$_2$CF$_3$, C$_{3-10}$ carbocycle, or a 5–14 membered heterocycle consisting of carbon atoms and 1–4 heteroatoms selected from the group consisting of N, O, and S(O)$_p$;

each R$^e$ is, independently at each occurrence, H, C$_{1-6}$ alkyl, C$_{1-6}$ alkoxy, phenoxy, benzoxy, C$_{3-10}$ carbocycle substituted with 0–2 R$^{c1}$, or a 5–10 membered heterocycle consisting of carbon atoms and 1–4 heteroatoms selected from the group consisting of N, O, and S(O)$_p$, and substituted with 0–2 R$_{c1}$;

m is 0, 1, 2 or 3;

n is 0, 1, 2, or 3;

each p is, independently at each occurrence, 0, 1, or 2;

each r is, independently at each occurrence, 0, 1, 2, 3, or 4;

each s is, independently at each occurrence, 0, 1, 2, 3, or 4; and each t is, independently at each occurrence, 2, 3, or 4.

2. A compound according to claim 1, wherein:

R$^1$ is Q, F, Cl, Br, I, CN, NO$_2$, —CF$_2$CF$_3$, —NR$^7$R$^8$, C$_{1-4}$ haloalkyl, —C$_{1-6}$ alkylene-Q, —C$_{2-6}$ alkenylene-Q, —C$_{2-6}$ alkynylene-Q, —(CR$^a$R$^{a1}$)$_t$O(CR$^a$R$^{a1}$)$_s$—Q, —(CR$^a$R$^{a1}$)$_t$NR$^a$(CR$^a$R$^{a1}$)$_s$—Q, —(CR$^a$R$^{a1}$)$_r$C(O)(CR$^a$R$^{a1}$)$_s$—Q, —(CR$^a$R$^{a1}$)$_r$C(O)O(CR$^a$R$^{a1}$)$_s$—Q, —(CR$^a$R$^{a1}$)$_r$OC(O)(CR$^a$R$^{a1}$)$_s$—Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$—Q, —(CR$^a$R$^{a1}$)$_r$NR$^a$C(O)(CR$^{aRa1}$)$_s$Q, -(CR$^a$R$^{a1}$)$_r$S(CR$^a$R$^{a1}$)$_s$-Q, —(CR$^a$R$^{a1}$)$_r$S(O)(CR$^a$R$^{a1}$)$_s$—Q, —(CR$^a$R$^{a1}$)$_r$S(O)$_2$(CR$^a$R$^{a1}$)$_s$—Q, —(CR$^a$R$^{a1}$)$_t$SO$_2$NR$^a$(CR$^a$R$^{a1}$)$_s$—Q, or —(CR$^a$R$^{a1}$)$_r$NR$^a$SO$_2$(CR$^a$R$^{a1}$)$_s$—Q;

R$^5$ is Q, —C$_{1-6}$ alkylene-Q, —C$_{2-6}$ alkenylene-Q, —C$_{2-6}$ alkynylene-Q, —(CR$^a$R$^{a1}$)$_t$O(CR$^a$R$^{a1}$)$_s$—Q, —(CR$^a$R$^{a1}$)$_t$NR$^a$(CR$^a$R$^{a1}$)$_s$—Q, —(CR$^a$R$^{a1}$)$_r$C(O)(CR$^a$R$^{a1}$)$_s$—Q, —(CR$^a$R$^{a1}$)$_r$C(O)O(CR$^a$R$^{a1}$)$_s$—Q, —(CR$^a$R$^{a1}$)$_r$OC(O)(CR$^a$R$^{a1}$)$_s$—Q, —(CR$^a$R$^{a1}$)$_r$C(O)NR$^a$R$^{a1}$, —(CR$^a$R$^{a1}$)$_r$C(O)NR$^a$(CR$^a$R$^{a1}$)$_s$—Q, —(CR$^a$R$^{a1}$)$_r$NR$^a$C(O)(CR$^a$R$^{a1}$)$_s$—Q, —(CR$^a$R$^{a1}$)$_r$S(CR$^a$R$^{a1}$)$_s$—Q, —(CR$^a$R$^{a1}$)$_r$S(O)(CR$^a$R$^{a1}$)$_s$—Q, —(CR$^a$R$^{a1}$)$_r$S(O)$_2$(CR$^a$R$^{a1}$)$_s$—Q, —(CR$^a$R$^{a1}$)$_t$SO$_2$NR$^a$(CR$^a$R$^{a1}$)$_s$—Q, or —(CR$^a$R$^{a1}$)$_r$NR$^a$SO$_2$(CR$^a$R$^{a1}$)$_s$—Q;

R$^6$ is H, —C$_{1-6}$ alkylene-Q, —C$_{2-6}$ alkenylene-Q, or —C$_{2-6}$ alkynylene-Q;

each R$^9$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$; or (CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

each R$^{10}$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$NR$^a$C(O)NR$^a$R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–2 R$^{c1}$, C$_{2-6}$ alkenyl substituted with 0–2 R$^{c1}$, C$_{2-6}$ alkynyl substituted with 0–2 R$^{c1}$, —(CR$^a$R$^{a1}$)$_r$—C$_{3-10}$ carbocycle substituted with 0–2 R$^{c1}$; or —(CR$^a$R$^{a1}$)$_r$-5–10 membered heterocycle consisting of carbon atoms and 1–4 heteroatoms selected from the group consisting of N, O, and S(O)$_p$, and substituted with 0–2 R$^{c1}$;

each Q is, independently at each occurrence, H, CF$_3$, —CH$_2$F, —CHF$_2$, C$_{1-6}$ alkyl, a C$_{3-10}$ carbocycle substituted with 0–5 R$^d$, or a 5–10 membered heterocycle consisting of carbon atoms and 1–4 heteroatoms selected from the group consisting of NR$^9$, O, and S(O)$_p$, and substituted with 0–5 R$^d$;

each Q$^1$ is, independently at each occurrence, C$_{1-6}$ alkyl, a C$_{3-10}$ carbocycle substituted with 0–5 R$^d$, or a 5–12 membered heterocycle consisting of carbon atoms and 1–4 heteroatoms selected from the group consisting of NR$^9$, O, and S(O)$_p$, and substituted with 0–5 R$^d$;

Z$^0$ is aryl or a 5–6 membered heteroaryl consisting of carbon atoms and 0–3 ring heteroatoms selected from O, N, NR$^9$, and S, and substituted with 0–3 R$^{10}$; and the aryl or heteroaryl is optionally fused to a 5–6 membered carbocycle or heterocycle consisting of carbon atoms and 0–2 ring heteroatoms selected from O, N, NR$^9$, and S(O)$_p$, and 0–2 double bonds, and substituted with 0–3 R$^{10}$;

W is (CR$^a$R$^{a1}$)$_m$, C$_{2-3}$ alkenylene, or C$_{2-3}$ alkynylene;

U is O, C(O), CR$^a$(OH), C(O)O, OC(O), C(O)NR$^{a1}$, S(O)$_p$, S(O)$_p$NR$^{a1}$, or NR$^{a1}$S(O)$_p$;

X is a bond or C$_{1-3}$ alkylene;

Y is a bond, O, NR$^{a1}$, S(O)$_p$, or C(O);

alternatively, Z$^0$ is absent, and W—U—X—Y forms S(O)$_p$;

Z is a C$_{3-8}$ cycloalkyl substituted with 0–5 R$^b$, a C$_{3-8}$ cycloalkenyl substituted with 0–5 R$^b$, phenyl substituted with 0–5 R$^b$, naphthyl substituted with 0–5 R$^b$ or a 5–14 membered heterocycle consisting of carbon atoms and 1–4 heteroatoms selected from the group consisting of N, O, and S(O)$_p$ and substituted with 0–5 R$^b$;

U$^a$ is a bond, O, NR$^{a1}$, C(O), CR$^a$(OH), C(O)O, C(O)NR$^{a1}$, NR$^{a1}$C(O), S(O)$_p$, S(O)$_p$NR$^{a1}$, or NR$^{a1}$S(O)$_p$;

X$^a$ is a bond, C$_{1-4}$ alkylene, C$_{2-4}$ alkenylene, or C$_{2-4}$ alkynylene;

Y$^a$ is a bond, O, or NR$^{a1}$;

Z$^a$ is a C$_{6-13}$ carbocycle substituted with 0–5 R$^c$, or a 5–14 membered heterocycle consisting of carbon atoms and 1–4 heteroatoms selected from the group consisting of N, O, and S(O)$_p$ and substituted with 0–5 R$^c$;

provided that U, Y, Z, U$^a$, Y$^a$, and Z$^a$ do not combine to form a N—N, N—O, O—N, O—O, S(O)$_p$—O, O—S(O)$_p$ or S(O)$_p$—S(O)$_p$ group;

each R$^c$ is, independently at each occurrence, H, Cl, F, Br, I, =O, CN, NO$_2$, CF$_3$, CF$_2$CF$_3$, CH$_2$F, CHF$_2$, —(CR$^a$R$^{a1}$)$_r$OR$^a$, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)R$^{a1}$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)$_p$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-6}$ alkyl substituted with 0–1 R$^{c1}$, C$_{2-6}$ alkenyl substituted with 0–1 R$^{c1}$, C$_{2-6}$ alkynyl substituted with 0–1 R$^{c1}$, —(CH$_2$)$_r$—C$_{3-6}$ carbocycle substituted with 0–2 R$^{c1}$, or —(CH$_2$)$_r$-5–6 membered heterocycle consisting of carbon atoms and 1–4 heteroatoms selected from the group consisting of N, O, and S(O)$_p$, and substituted with 0–2 R$^{c1}$;

alternatively, when two R$^c$ groups are attached to the same carbon atom, they form a 3–8 membered carbocyclic or heterocyclic spiro ring C substituted with 0–2 R$^{c1}$ and consisting of carbon atoms, 0–4 ring heteroatoms selected from O, N, and S(O)$_p$, and 0–2 double bonds, provided that ring C contains other than a S—S, O—O, or S—O bond;

alternatively, when two R$^c$ groups are attached to adjacent carbon atoms, together with the carbon atoms to which they are attached they form a 5–7 membered carbocyclic or heterocyclic ring D substituted with 0–2 R$^{c1}$ and consisting of carbon atoms, 0–2 heteroatoms selected from the group consisting of N, O, and S(O)$_p$, and 0–3 double bonds; and each R$^d$ is, independently at each occurrence, C$_{1-6}$ alkyl, OR$^a$, Cl, F, I, =O, CN, NO$_2$, NR$^a$R$^{a1}$, C(O)R$^a$, —C(O)OR$^a$, —C(O)NR$^a$R$^{a1}$, —S(O)$_2$NR$^a$R$^{a1}$, —NR$^a$S(O)$_2$R$^{a3}$, —S(O)$_p$R$^{a3}$, CF$_3$, C$_{3-6}$ carbocycle, or a 5–6 membered heterocycle consisting of carbon atoms and 1–4 heteroatoms selected from the group consisting of N, O, and S(O)$_p$.

3. A compound according to claim 2, wherein:

R$^1$ is Q, F, Cl, CN, —NR$^7$R$^8$, C$_{1-4}$ haloalkyl, —C$_{1-4}$ alkylene-Q, —C$_{2-4}$ alkenylene-Q, —C$_{2-4}$ alkynylene-Q, —(CR$^a$R$^{a1}$)$_t$O(CR$^a$R$^{a1}$)$_s$—Q, —(CR$^a$R$^{a1}$)$_t$NR$^a$(CR$^a$R$^{a1}$)$_s$—Q, —(CR$^a$R$^{a1}$)$_t$C(O)(CR$^a$R$^{a1}$)$_s$—Q, —(CR$^a$R$^{a1}$)$_t$C(O)O(CR$^a$R$^{a1}$)$_s$—Q, —(CR$^a$R$^{a1}$)$_t$C(O)NR$^a$R$_{a1}$, —(CR$^a$R$^{a1}$)$_t$C(O)NR$_a$(CR$^a$R$^{a1}$)$_s$—Q, —(CR$^a$R$^{a1}$)$_t$S(CR$^a$R$^{a1}$)$_s$—Q, —(CR$^a$R$^{a1}$)$_t$S(O)(CR$^a$R$^{a1}$)$_s$—Q, —(CR$^a$R$^{a1}$)$_t$S(O)$_2$(CR$^a$R$^{a1}$)$_s$—Q, —(CR$^a$R$^{a1}$)$_t$SO$_2$NR$^a$(CR$^a$R$^{a1}$)$_s$—Q, or —(CR$^a$R$^{a1}$)$_t$NR$^a$SO$_2$(CR$^a$R$^{a1}$)$_s$—Q;

R$^2$ is H or C$_{1-4}$ alkyl;

R$^3$ is H or C$_{1-4}$ alkyl;

R$^5$ is Q, C$_{1-4}$ alkyl, C$_{2-4}$ alkenyl, C$_{2-4}$ alkynyl, —(CH$_2$)$_t$O(CH$_2$)$_s$—Q, —(CH$_2$)$_r$NR$^a$(CH$_2$)$_s$—Q, —(CH$_2$)$_r$C(O)(CH$_2$)$_s$—Q, —(CH$_2$)$_r$C(O)O(CH$_2$)$_s$—Q, —(CH$_2$)$_r$OC(O)(CH$_2$)$_s$—Q, —(CH$_2$)$_r$C(O)NR$^a$R$^{a1}$, —(CH$_2$)$_r$C(O)NR$^a$(CH$_2$)$_s$—Q, —(CH$_2$)$_r$NR$^a$C(O)(CH$_2$)$_s$—Q, —(CH$_2$)$_r$S(CH$_2$)$_s$—Q, —(CH$_2$)$_r$S(O)(CH$_2$)$_s$—Q, —(CH$_2$)$_r$S(O)$_2$(CH$_2$)$_s$—Q, —(CH$_2$)$_r$SO$_2$NR$^a$(CH$_2$)$_s$—Q, or —(CH$_2$)$_r$NR$^a$SO$_2$(CH$_2$)$_s$—Q;

R$^6$ is H, —C$_{1-4}$ alkyl, C$_{2-4}$ alkenyl, or C$_{2-4}$ alkynyl;

R$^7$ is H, C$_{1-4}$ alkyl, C$_{2-4}$ alkenyl, C$_{2-4}$ alkynyl, —(CR$^a$R$^{a1}$)$_r$C(O)(CR$^a$R$^{a1}$)$_s$—Q$^1$, —(CR$^a$R$^{a1}$)$_r$C(O)O(CR$^a$R$^{a1}$)$_s$—Q$^1$, —(CR$^a$R$^{a1}$)$_r$C(O)O(CR$^a$R$^{a1}$)$_r$OC(O)$_s$—Q$^1$, —(CR$^a$R$^{a1}$)$_r$C(O)NH(CR$^a$R$^{a1}$)$_s$—Q$^1$, or —(CR$^a$R$^{a1}$)$_r$S(O)$_2$)(CR$^a$R$^{a1}$)$_s$—Q$^1$;

R$^8$ is H, C$_{1-4}$ alkyl, or —(CH$_2$)$_n$-phenyl;

each R$^9$ is, independently at each occurrence, H, —(CR$^a$R$^{a1}$)$_t$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-4}$ alkyl substituted with 0–1 R$^{c1}$, C$_{2-4}$ alkenyl substituted with 0–1 R$^{c1}$, C$_{2-4}$ alkynyl substituted with 0–1 R$^{c1}$, —(CH$_2$)$_r$—C$_{3-10}$ carbocycle substituted with 0–2 R$^{c1}$; or —(CH$_2$)$_r$-5–10 membered heterocycle consisting of carbon atoms and 1–4 heteroatoms selected from the group consisting of N, O, and S(O)$_p$, and substituted with 0–2 R$^{c1}$;

each R$^{10}$ is, independently at each occurrence, H, —(CR$^a$R$^{a1}$)$_r$NR$^a$R$^{a1}$, —(CR$^a$R$^{a1}$)$_r$C(O)NR$^a$OH, —(CR$^a$R$^{a1}$)$_r$C(O)(CR$^a$R$^{a1}$)$_s$R$^e$, —(CR$^a$R$^{a1}$)$_r$C(O)OR$^{a1}$, —(CR$^a$R$^{a1}$)$_r$C(O)NR$^a$R$^{a1}$, —(CR$^a$R$^{a1}$)$_r$NR$^a$C(O)R$^{a1}$, —(CR$^a$R$^{a1}$)$_r$S(O)R$^{a3}$, —(CR$^a$R$^{a1}$)$_r$S(O)R$^{a3}$, —(CR$^a$R$^{a1}$)$_r$S(O)$_2$R$^{a3}$, —(CR$^a$R$^{a1}$)$_r$SO$_2$NR$^a$R$^{a1}$, —(CR$^a$R$^{a1}$)$_r$NR$^a$SO$_2$R$^{a3}$, C$_{1-4}$ alkyl substituted with 0–1 R$^{c1}$, C$_{2-4}$ alkenyl substituted with 0–1 R$^{c1}$, C$_{2-4}$ alkynyl substituted with 0–1 R$^{c1}$, —(CH$_2$)$_r$—C$_{3-10}$ carbocycle substituted with 0–2 R$^{c1}$; or —(CH$_2$)$_r$-5–10 membered heterocycle consisting of carbon atoms and 1–4 heteroatoms selected from the group consisting of N, O, and S(O)$_p$, and substituted with 0–2 R$^{c1}$;

Z$^0$ is phenyl substituted with 0–3 R$^{10}$, or a 5–6 membered heteroaryl substituted with 0–3 R$^{10}$ and selected from: oxazolyl, isoxazolyl, thiazolyl, isothiazolyl, imidazolyl, pyrrolyl, furanyl, thienyl, pyridyl, pyrimidinyl, pyridazinyl, pyrazinyl, or pyrazolyl;

W is (CH$_2$)$_m$;

U is O, C(O), CR$^a$(OH), C(O)NR$^{a1}$, S(O)$_p$, S(O)$_p$NR$^{a1}$, or NR$^{a1}$S(O)$_p$;

X is a bond, or methylene or ethylene;

Y is a bond, O, NR$^{a1}$, S(O)$_p$, or C(O);

alternatively, Z$^0$ is absent, and W—U—X—Y forms S(O)$_p$;

$U^a$ is a bond, O, $NR^{a1}$, C(O), $C(O)NR^{a1}$, $NR^{a1}C(O)$, $S(O)_p$, $S(O)_pNR^{a1}$, or $NR^{a1}S(O)_p$;

each $R^c$ is, independently at each occurrence, H, Cl, F, Br, I, =O, CN, $NO_2$, $CF_3$, $CH_2F$, $CHF_2$, $—(CR^aR^{a1})_rOR^a$, $—(CR^aR^{a1})_rNR^aR^{a1}$, $—(CR^aR^{a1})_rC(O)R^{a1}$, $—(CR^aR^{a1})_rC(O)OR^{a1}$, $—(CR^aR^{a1})_rC(O)NR^aR^{a1}$, $—(CR^aR^{a1})_rNR^aC(O)R^{a1}$, $—(CR^aR^{a1})_rS(O)_pR^{a3}$, $—(CR^aR^{a1})_rSO_2NR^aR^{a1}$, $—(CR^aR^{a1})_rNR^aSO_2R^{a3}$, $C_{1-6}$ alkyl, $C_{2-6}$ alkenyl, $C_{2-6}$ alkynyl, $—(CH_2)_r$—$C_{3-6}$ cycloalkyl substituted with 0–1 $R^{c1}$, phenyl substituted with 0–2 $R^{c1}$, or $—(CH_2)_r$-5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–7 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds;

each $R^d$ is, independently at each occurrence, $C_{1-6}$ alkyl, $OR^a$, Cl, F, Br, I, =O, $NR^aR^{a1}$, $C(O)R^a$, $—C(O)OR^a$, $—C(O)NR^aR^{a1}$, $—S(O)_2NR^aR^{a1}$, $—NR^aS(O)_2R^{a3}$, $—S(O)_pR^{a3}$, $CF_3$, or phenyl;

m is 0, 1, or 2;

n is 0, 1, or 2;

each r is, independently at each occurrence, 0, 1, 2, or 3;

each s is, independently at each occurrence, 0, 1, 2, or 3; and each t is, independently at each occurrence, 2, or 3.

4. A compound according to claim 3, wherein:

A is O;

$R^1$ is Q, F, Cl, CN, $—NR^7R^8$, $C_{1-4}$ haloalkyl, $—C_{1-4}$ alkylene-Q, $—C_{2-4}$ alkenylene-Q, $—C_{2-4}$ alkynylene-Q, $—(CH_2)_rO(CH_2)_s—Q$, $—(CH_2)_rNR^a(CH_2)_s—Q$, $—(CH_2)_rC(O)(CH_2)_s—Q$, $—(CH_2)_rC(O)O(CH_2)_s—Q$, $—(CH_2)_rC(O)NR^aR^{a1}$, $—(CH_2)_rC(O)NR^a(CH_2)_s—Q$, $—(CH_2)_rS(CH_2)_s—Q$, $—(CH_2)_rS(O)(CH_2)_s—Q$, $—(CH_2)_rS(O)_2(CH_2)_s—Q$, $—(CH_2)_rSO_2NR^a(CH_2)_s—Q$, or $—(CH_2)_rNR^aSO_2(CH_2)_s—Q$;

$R^5$ is H, $C_{1-4}$ alkyl, $C_{2-4}$ alkenyl, or $C_{2-4}$ alkynyl;

$R^7$ is H, $C_{1-4}$ alkyl, or $—(CH_2)_n$-phenyl;

$R^8$ is H, $C_{1-4}$ alkyl, or $—(CH_2)_n$-phenyl;

each $R^9$ is, independently at each occurrence, H, $—(CH_2)_t$ $NR^aR^{a1}$, $—(CH_2)_rC(O)(CH_2)_sR^e$, $—(CH_2)_rC(O)OR^{a1}$, $—(CH_2)_rC(O)NR^aR^{a1}$, $—(CH_2)_rNR^aC(O)R^{a1}$, $—(CH_2)_rS(O)R^{a3}$, $—(CH_2)_rS(O)R^{a3}$, $—(CH_2)_rS(O)_2R^{a3}$, $—(CH_2)SO_2NR^aR^{a1}$, $—(CH_2)_rNR^aSO_2R^{a3}$, $C_{1-4}$ alkyl, or $—(CH_2)_n$-phenyl;

each $R^{10}$ is, independently at each occurrence, H, $—(CH_2)_rNR^aR^{a1}$, $—(CH_2)_rC(O)(CH_2)_sR^e$, $—(CH_2)_rC(O)OR^{a1}$, $—(CH_2)_rC(O)NR^aR^{a1}$, $—(CH_2)_rNR^aC(O)R^{a1}$, $—(CH_2)_rS(O)R^{a3}$, $—(CH_2)_rS(O)R^{a3}$, $—(CH_2)_rS(O)_2R^{a3}$, $—(CH_2)_rSO_2NR^aR^{a1}$, $—(CH_2)_rNR^aSO_2R^{a3}$, $C_{1-4}$ alkyl, or $—(CH_2)_n$-phenyl;

$Z^0$ is phenyl substituted with 0–2 $R^{10}$, or pyridyl substituted with 0–2 $R^{10}$;

alternatively, $Z^0$ is absent, and W—U—X—Y forms $S(O)_p$;

U is O, C(O), CH(OH), C(O)NH, $S(O)_p$, $S(O)_pNH$, or $NHS(O)_p$;

Z is a $C_{4-8}$ cycloalkyl substituted with 0–3 $R^b$, a $C_{4-8}$ cycloalkenyl substituted with 0–3 $R^b$, phenyl substituted with 0–4 $R^b$, naphthyl substituted with 0–5 $R^b$, or a heterocycle substituted with 0–3 $R^b$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, and quinazolinyl;

$Z^a$ is phenyl substituted with 0–3 $R^c$, naphthyl substituted with 0–3 $R^c$, or a heterocycle substituted with 0–3 $R^c$ and selected from the group: furanyl, tetrahydrofuranyl, thiazolyl, oxazolyl, imidazolyl, isothiazolyl, isoxazolyl, 4,5-dihydro-isoxazolyl, thienyl, triazolyl, thiadiazolyl, oxadiazolyl, pyridyl, pyrimidinyl, piperazinyl, piperidinyl, pyranyl, pyrazinyl, pyrazolyl, pyridoimidazolyl, pyrrolidinyl, pyrrolyl, indolyl, indolinyl, benzimidazolyl, benzothiazinyl, benzofuranyl, benzothiophenyl, benzoxazolyl, benzthiazolyl, benztriazolyl, benzisoxazolyl, benzisothiazolyl, quinolinyl, tetrahydroquinolinyl, isoquinolinyl, tetrahydro-isoquinolinyl, indazolyl, isobenzofuranyl, isoindazolyl, isoindolinyl, isoindolyl, methylenedioxyphenyl, quinazolinyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, and pyrazolo[1,5-a]pyridinyl;

each $R^c$ is, independently at each occurrence, H, Cl, F, Br, =O, $CF_3$, $CH_2F$, $CHF_2$, $—(CR^aR^{a1})_rOR^a$, $—(CR^aR^{a1})_rNR^aR^{a1}$, $—(CR^aR^{a1})_rC(O)R^{a1}$, $—(CR^aR^{a1})_rC(O)OR^{a1}$, $—(CR^aR^{a1})_rC(O)NR^aR^{a1}$, $—(CR^aR^{a1})_rNR^aC(O)R^{a1}$, $—(CR^aR^{a1})_rS(O)_pR^{a3}$, $—(CR^aR^{a1})_rSO_2NR^aR^{a1}$, $—(CR^aR^{a1})_rNR^aSO_2R^{a3}$, $C_{1-6}$ alkyl, $C_{2-6}$ alkenyl, $C_{2-6}$ alkynyl, phenyl substituted with 0–2 $R^{c1}$, or a 5–6 membered heterocycle consisting of carbon atoms and 1–4 heteroatoms selected from the group consisting of N, O, and $S(O)_p$, and substituted with 0–2 $R^{c1}$;

alternatively, when two $R^c$ groups are attached to adjacent carbon atoms, together with the carbon atoms to which they are attached they form a 5–6 membered carbocyclic or heterocyclic ring D substituted with 0–2 $R^{c1}$ and consisting of carbon atoms, 0–2 heteroatoms selected from the group consisting of N, O, and $S(O)_p$, and 0–3 double bonds; and each $R^d$ is, independently at each occurrence, $C_{1-6}$ alkyl, $OR^a$, Cl, F, Br, I, =O, $NR^aR^{a1}$, $C(O)R^a$, $—C(O)OR^a$, $—C(O)NR^aR^{a1}$, $—S(O)_2NR^aR^{a1}$, $—NR^aS(O)_2R^{a3}$, $—S(O)_pR^{a3}$, $CF_3$, or phenyl.

5. A compound according to claim 4, wherein:

A is O;

L is a bond, CO or $CH_2$;

$R^1$ is H, $C_{1-4}$ haloalkyl, $C_{1-4}$ alkyl, or $—C(O)O(CH_2)_s—$H;

$Z^0$ is phenyl;

alternatively, $Z^0$ is absent, and W—U—X—Y forms $S(O)_p$;

Z is phenyl substituted with 0–2 $R^b$;

$Z^a$ is phenyl substituted with 0–3 $R^c$, naphthyl substituted with 0–3 $R^c$, or a heterocycle substituted with 0–3 $R^c$ and selected from the group: pyridyl, quinolinyl, imidazolyl, benzimidazolyl, indolyl, 1,1-dioxido-2,3-dihydro-4H-1,4-benzothiazin-4-yl, 1,1-dioxido-3,4-dihydro-2H-1-benzothiopyran-4-yl, 3,4-dihydro-2H-chromen-4-yl, 2H-chromen-4-yl, pyrazolyl, and pyrazolo[1,5-a]pyridinyl;

each $R^b$ is, independently at each occurrence, $C_{1-6}$ alkyl, —$OR^a$, Cl, F, Br, —$NR^aR^{a1}$, —$C(O)R^a$, —$C(O)OR^a$, —$C(O)NR^aR^{a1}$, —$S(O)_2NR^aR^{a1}$, —$NR^aS(O)_2R^{a3}$, —$S(O)_pR^{a3}$, or $CF_3$;

each $R^c$ is, independently at each occurrence, H, $C_{1-6}$ alkyl, $C_{2-6}$ alkenyl, $C_{2-6}$ alkynyl, Cl, F, Br, =O, $CF_3$, —$(CH_2)_rOR^a$, —$(CH_2)_rNR^aR^{a1}$, —$(CH_2)_rC(O)R^{a1}$, —$(CH_2)_rC(O)OR^{a1}$, —$(CH_2)_rC(O)NR^aR^{a1}$, —$(CH_2)_rNR^aC(O)R^{a1}$, —$(CH_2)_rS(O)_pR^{a3}$, —$(CH_2)_rSO_2NR^aR^{a1}$, or —$(CH_2)_rNR^aSO_2R^{a3}$;

alternatively, when two $R^c$ groups are attached to adjacent carbon atoms, together with the carbon atoms to which they are attached they form a 5–6 membered carbocyclic or heterocyclic ring consisting of: carbon atoms and 0–1 heteroatoms selected from the group consisting of N, O, and $S(O)_p$; and each $R^e$ is, independently at each occurrence, H, $C_{1-6}$ alkyl, $C_{1-6}$ alkoxy, phenoxy, benzoxy, phenyl substituted with 0–1 $R^{c1}$, or a 5–6 membered heterocycle consisting of carbon atoms and 1–4 heteroatoms selected from the group consisting of N, O, and $S(O)_p$, and substituted with 0–1 $R^{c1}$.

6. A compound selected from the group:
4-(2-methyl-quinolin-4-yl methoxy)-N-[2-(2-oxo-2,3-dihydro-1H-imidazole-4-carbonyl)phenyl]benzamide;
4-(2-methyl-quinolin-4-yl methyl)-N-[2-(2-oxo-2,3-dihydro-1H-imidazole-4-carbonyl)phenyl]benzamide;
4-(2-methyl-quinolin-4-yl methoxy)-N-[2-(2-oxo-2,3-dihydro-1H-imidazol-4-yl methyl)phenyl]benzamide;
5-[4-(2-methyl-quinolin-4-ylmethoxy)-benzenesulfonylmethyl]-2-oxo-2,3-dihydro-1H-imidazole-4-carboxylic acid methyl ester;
4-[4-(2-methyl-quinolin-4-ylmethoxy)-phenylsulfanylmethyl]-1,3-dihydro-imidazol-2-one;
4-[4-(2-methyl-quinolin-4-ylmethoxy)-benzenesulfinylmethyl]-1,3-dihydro-imidazol-2-one; and
4-[4-(2-methyl-quinolin-4-ylmethoxy)-benzenesulfonylmethyl]-1,3-dihydro-imidazol-2-one;

or a stereoisomer or pharmaceutically acceptable salt or solvate thereof.

7. A pharmaceutical composition, comprising: a pharmaceutically acceptable carrier and a therapeutically effective amount of a compound according to claim 1, or a stereoisomer or pharmaceutically acceptable salt or solvate form thereof.

8. A pharmaceutical composition, comprising: a pharmaceutically acceptable carrier and a therapeutically effective amount of a compound according to claim 2, or a stereoisomer or pharmaceutically acceptable salt or solvate form thereof.

9. A pharmaceutical composition, comprising: a pharmaceutically acceptable carrier and a therapeutically effective amount of a compound according to claim 3, or a stereoisomer or pharmaceutically acceptable salt or solvate form thereof.

10. A pharmaceutical composition, comprising: a pharmaceutically acceptable carrier and a therapeutically effective amount of a compound according to claim 4, or a stereoisomer or pharmaceutically acceptable salt or solvate form thereof.

11. A pharmaceutical composition, comprising: a pharmaceutically acceptable carrier and a therapeutically effective amount of a compound according to claim 5, or a stereoisomer or pharmaceutically acceptable salt or solvate form thereof.

12. A pharmaceutical composition, comprising: a pharmaceutically acceptable carrier and a therapeutically effective amount of a compound according to claim 6, or a stereoisomer or pharmaceutically acceptable salt or solvate form thereof.

* * * * *